(12) United States Patent
Vilser

(10) Patent No.: US 7,281,800 B2
(45) Date of Patent: Oct. 16, 2007

(54) DEVICE AND METHOD FOR IMAGING, STIMULATION, MEASUREMENT AND THERAPY, IN PARTICULAR FOR THE EYE

(75) Inventor: Walthard Vilser, Rudolstadt (DE)

(73) Assignee: Imedos-Intelligente Optische Systeme der Medizin- und Messtechnik GmbH, Weimar (DE)

(*) Notice: Subject to any disclaimer, the term of this patent is extended or adjusted under 35 U.S.C. 154(b) by 680 days.

(21) Appl. No.: 10/250,498

(22) PCT Filed: Jan. 3, 2002

(86) PCT No.: PCT/DE02/00015

§ 371 (c)(1),
(2), (4) Date: Jul. 2, 2003

(87) PCT Pub. No.: WO02/053020

PCT Pub. Date: Jul. 11, 2002

(65) Prior Publication Data
US 2004/0051847 A1    Mar. 18, 2004

(30) Foreign Application Priority Data
Jan. 3, 2001    (DE) ............... 101 00 032

(51) Int. Cl.
*A61B 3/00* (2006.01)
*A61B 3/10* (2006.01)

(52) U.S. Cl. ............... 351/221; 351/246
(58) Field of Classification Search .......... 351/205, 351/211, 214, 221, 246
See application file for complete search history.

(56) References Cited

U.S. PATENT DOCUMENTS

| | | | |
|---|---|---|---|
| 5,233,373 A * | 8/1993 | Peters et al. | 351/221 |
| 5,337,106 A * | 8/1994 | Jutamulia et al. | 396/447 |
| 5,396,303 A * | 3/1995 | Peters et al. | 351/221 |
| 5,640,220 A * | 6/1997 | Vo et al. | 351/213 |
| 5,861,940 A * | 1/1999 | Robinson et al. | 351/221 |
| 5,867,251 A * | 2/1999 | Webb | 351/221 |
| 5,900,923 A | 5/1999 | Prendergast et al. | |
| 5,945,670 A * | 8/1999 | Rudeen | 250/235 |
| 5,953,082 A | 9/1999 | Butcher | |
| 6,000,800 A * | 12/1999 | Webb et al. | 351/211 |
| 6,003,993 A * | 12/1999 | Webb | 351/221 |
| 6,099,125 A * | 8/2000 | Webb et al. | 351/211 |
| 6,616,279 B1 * | 9/2003 | Davis et al. | 351/246 |
| 2003/0210378 A1 * | 11/2003 | Riza | 351/205 |

FOREIGN PATENT DOCUMENTS

| | | |
|---|---|---|
| DE | 38 39 272 | 9/1989 |
| DE | 196 48 935 | 5/1998 |
| EP | 0 645 825 | 3/1995 |
| EP | 1 183 992 | 3/2002 |

* cited by examiner

Primary Examiner—Hung Xuan Dang
(74) Attorney, Agent, or Firm—Reed Smith LLP

(57) ABSTRACT

Apparatuses whose system parameters and operation can be adapted in particular to a wide range of applications for imaging, testing, stimulating, measuring and treating the eye for carrying out a wide variety of examination tasks or treatment tasks substantially without taking technical steps in the manufacturing process through the control of beam manipulation units—EMS whose elements are independently controllable and which are in marked planes of the optical arrangement of the apparatus; methods for operating apparatuses of this type.

49 Claims, 22 Drawing Sheets

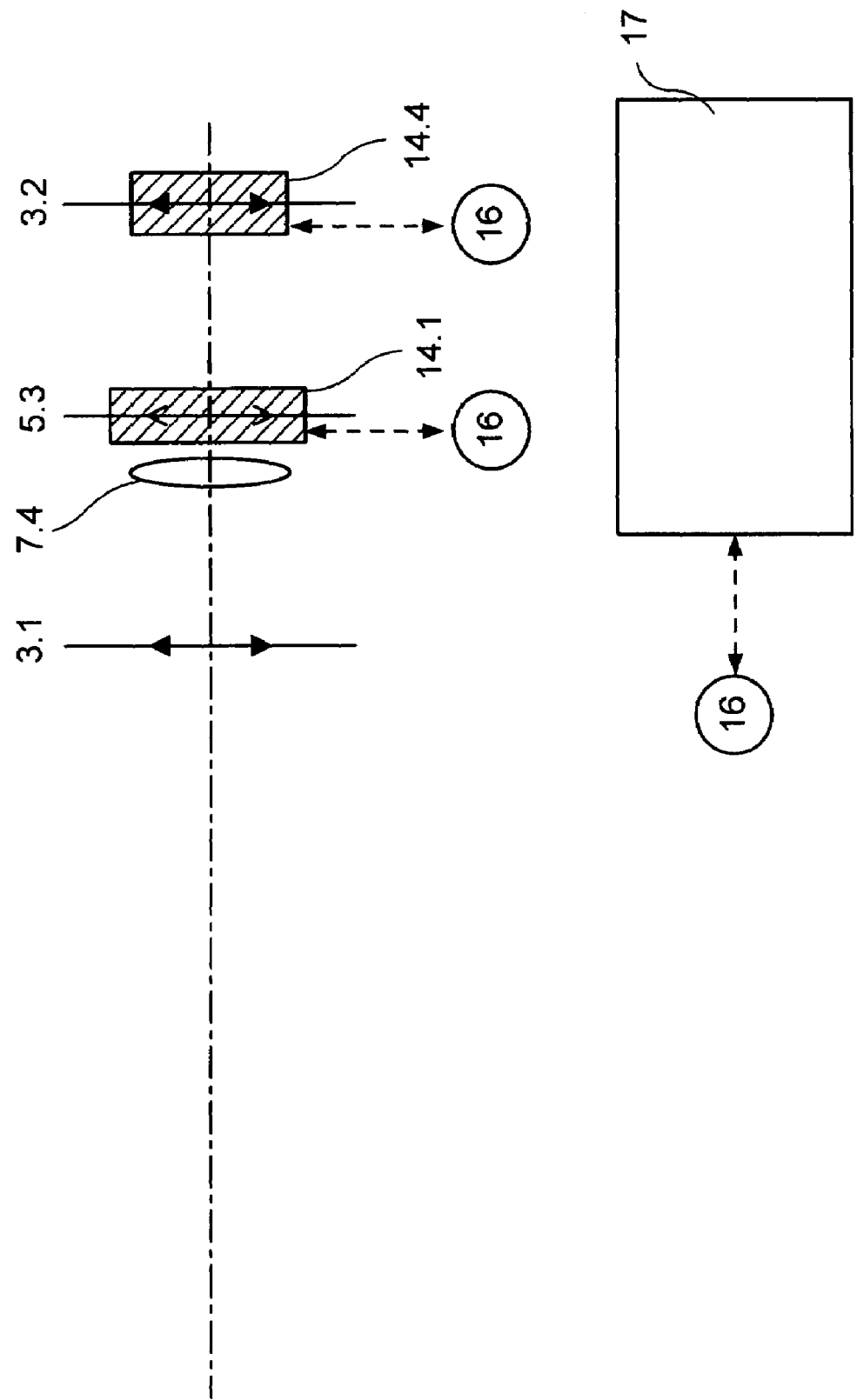

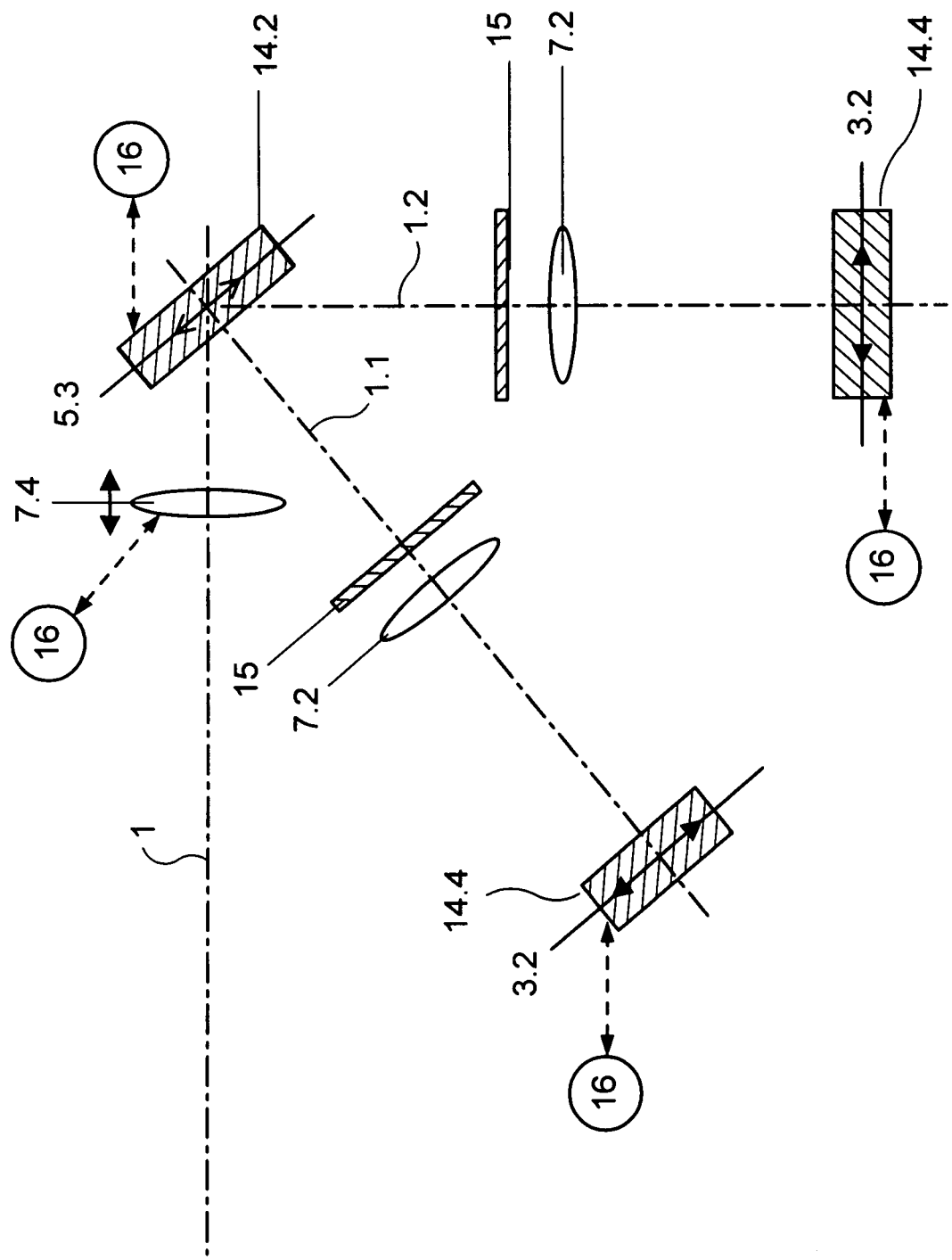

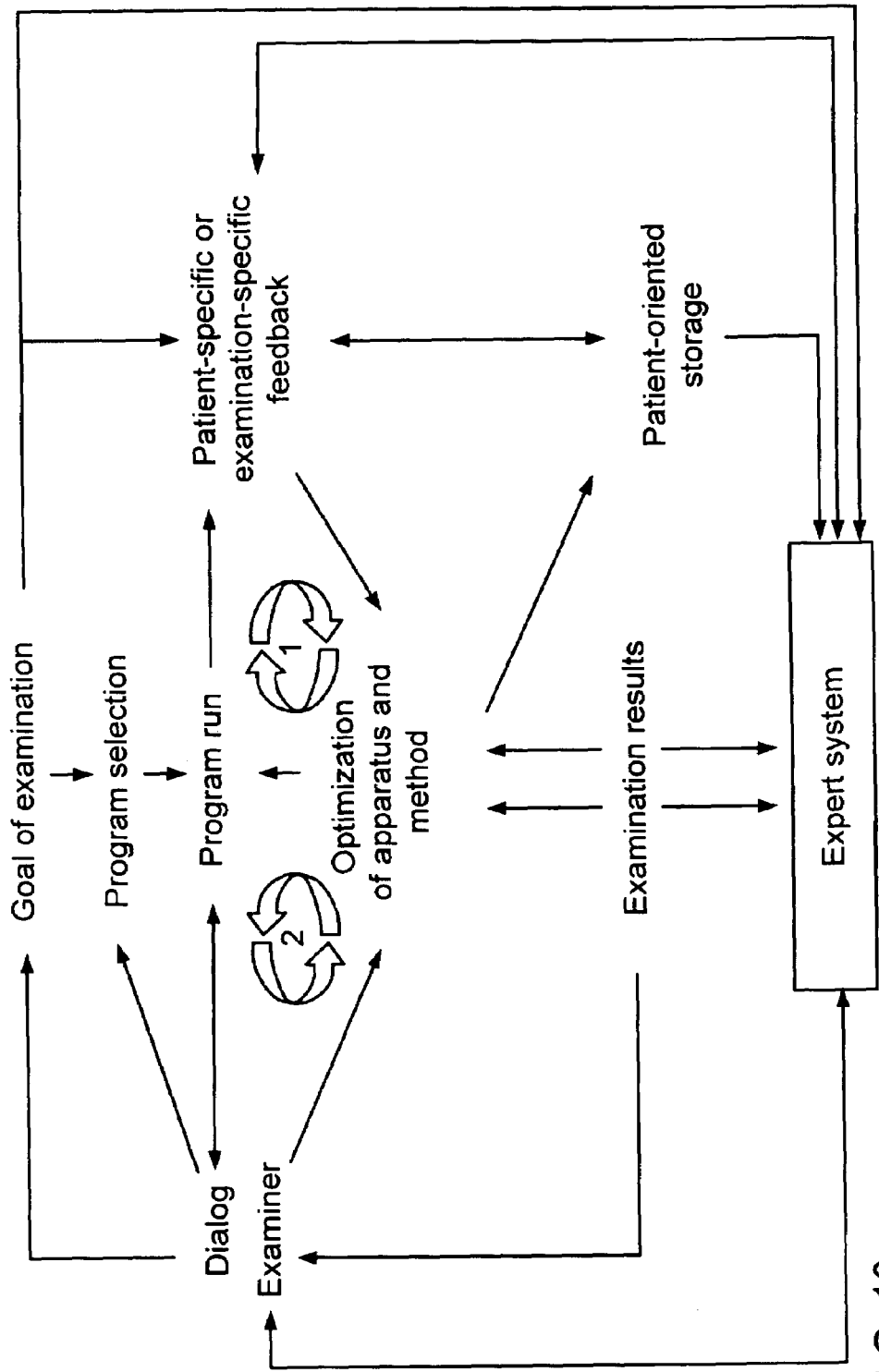
F I G. 10

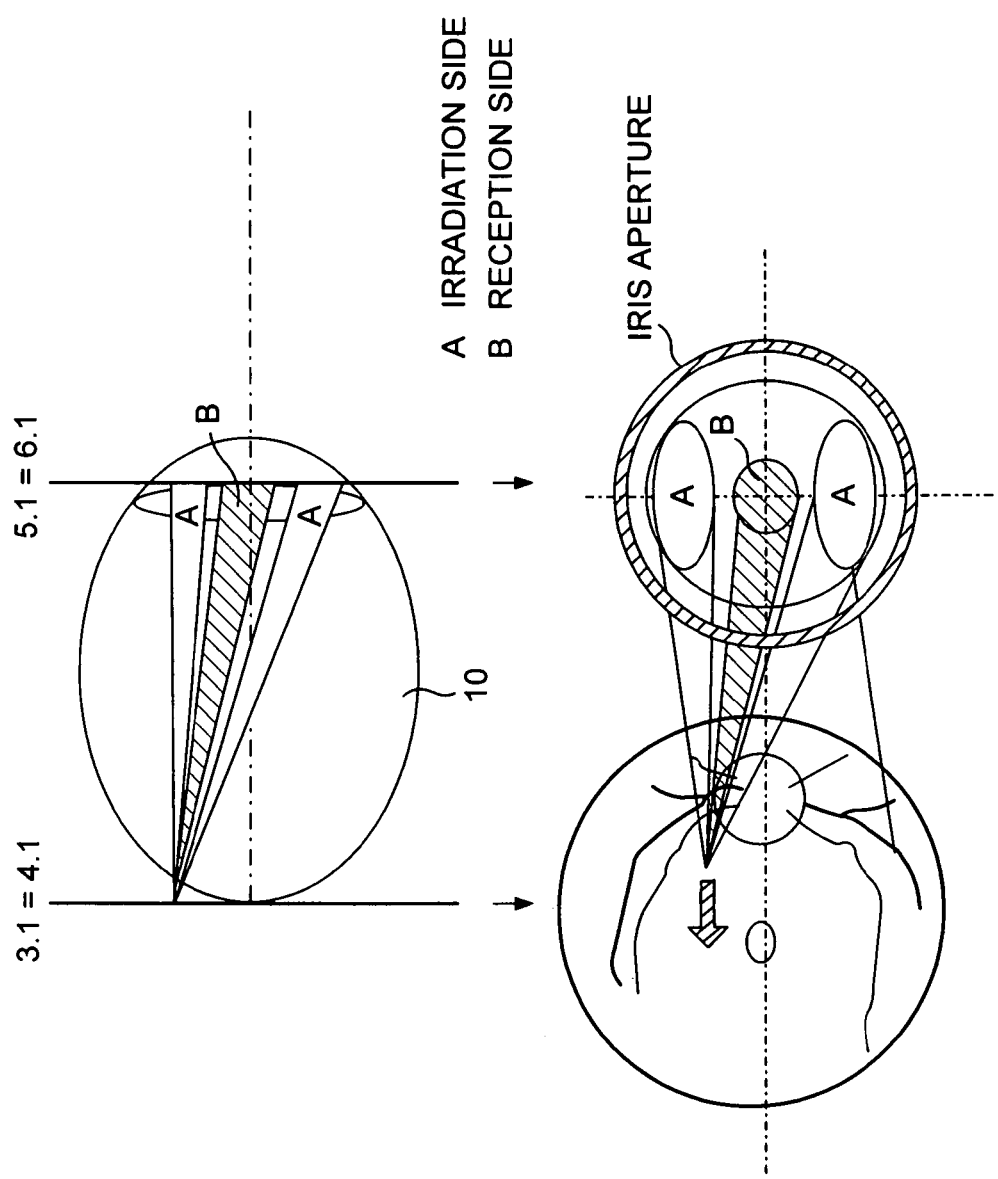
F I G. 15

DEVICE AND METHOD FOR IMAGING, STIMULATION, MEASUREMENT AND THERAPY, IN PARTICULAR FOR THE EYE

CROSS-REFERENCE TO RELATED APPLICATIONS

This application claims priority of International Application No. PCT/DE02/00015, filed Jan. 3, 2002 and German Application No. 101 00 032.4, filed Jan. 3, 2001, the complete disclosures of which are hereby incorporated by reference.

BACKGROUND OF THE INVENTION a) Field of the Invention

The invention is directed to apparatuses and methods for the examination and treatment of the eye in ophthalmology and optometry and, further, can be used commercially in medicine for the examination and treatment of tissue and for devices for imaging, measuring, testing and materials machining.

b) Description of the Related Art

At present, different systems are used for imaging (e.g., retinal cameras with photographic and electronic image acquisition, laser scanners, photography slit lamps), for testing purposes (e.g., perimetry systems, electrophysiological systems, microperimetry, visual acuity testing systems, including phoropters), for measurement (e.g., HRT, flow meters, GDX, refractometers, RVA), and for therapy for the eye (laser coagulation, PDT systems, etc.).

The disadvantage in all of the systems consists in the solution which is predetermined by principle and which is rigid in terms of optical design and which determines the systems already during their manufacture with respect to the purpose of application allowing only limited leeway for the adjustment of application characteristics (e.g., technical measurement properties or imaging properties).

As a result, different tasks in the examination and treatment of the eye require different measurement systems and therapy systems with a proportionately high investment and space requirement, and it is not possible to adapt in a flexible manner to variable application requirements and particularly to the individual distinctive features of the eye.

Particularly for measurement systems used for the eye, adapting to the individual peculiarities of each eye is frequently an essential precondition for eliminating or limiting sources of error or even the precondition for results capable of evaluation.

New systems have been developed for purposes of measuring and testing the eye through add-on modules or modifications of known conventional technology (e.g., add-on modules for the retinal camera). As a result of the compromises ensuing from this with respect to optical design solutions and electronic solutions, the new systems are not optimally tailored to the tasks and often cause unnecessarily high costs, limited practicability and, above all, very restricted application characteristics.

OBJECT AND SUMMARY OF THE INVENTION

It is the primary object of the invention to provide an apparatus whose system parameters and operation can be adapted by the user to a wide range of applications for imaging, testing, stimulating, measuring and treating the eye for carrying out a wide variety of examination tasks or treatment tasks substantially without taking technical steps in the manufacturing process.

Further, the system parameters of the apparatus are to be adjustable in optimal manner to the individual distinctive features of the eye being examined and/or treated.

It is also the object of the invention to provide an apparatus whose system parameters and operation can be adjusted and altered in a differentiated manner with respect to time and space in order to be able to carry out different examinations and treatments simultaneously.

Another object of the invention is to propose methods for operating an apparatus according to the invention which leads to improved examination results and treatment results.

The object of the invention is met in one form of the invention substantially in that beam manipulation units with independently controllable elements EMS are arranged in designated planes in the optical arrangement of the apparatus, each of these elements being connected via an interface to an information technology system ITS which controls the individual elements of the EMS so as to manipulate the characteristics of the beam in such a way that different beam paths can be generated with respect to time and space through programming technique.

Other advantageous constructions of an apparatus according to the invention are encompassed which differ from one another especially with respect to their functional adaptivity.

The object of the invention is also met for a method for operating an apparatus substantially in that elemental beam bundles are formed by controlling the elements of the EMS with respect to time and space. Different function-determining characteristics can be assigned to the elemental beam bundles simultaneously or successively, so that the elemental beam bundles can be allocated individually or in groups to a large number of different beam paths which can be generated by programming and which have different functions for different methods of imaging, testing, stimulation or therapy realized simultaneously and/or successively.

The totality of characteristics of an apparatus according to the invention operated according to the invention is substantially formed by the generated elemental beam bundles whose characteristics can be programmed individually with respect to possible parameters of the light (e.g., aperture geometry, field geometry, wavelength, intensity, direction and degree of polarization), the position of the pass points through the designated planes of the optical arrangement of the apparatus, and their sequence in time relative to one another (in succession or in parallel). A large number of functions of different conventional ophthalmological instrument systems can be realized in one individual apparatus by programming, i.e., examinations which are conventionally carried out with different systems can be realized simultaneously or in immediate succession without having to change the position of the patient in front of the instrument.

Due to the possibility of allocating characteristics to the elemental beam bundles individually by controlling the EMS and other controllable units of the apparatus, any beam paths can be generated so that the apparatus can be adapted with high functional adaptivity to the different aims of examination and treatment and with high individual adaptivity to the object being examined, particularly the eye of the patient and to the needs of the user. By programming different combinations of different beam paths and their timing, function tests and various examinations can be carried out in parallel and, therefore, errors in examination which are brought about by time differences between the examinations (altered marginal conditions between two examinations) can be eliminated.

New possibilities are opened up for functional diagnostics due to the possibility of combining examinations and stimulation (provocation).

The controllability of the beam paths makes it possible to examine volume units or surfaces in the eye which differ over time, location and spectrum and also makes it possible to minimize light stress.

A substantial marketing advantage consists in that only one apparatus must be physically purchased and the desired applications can be enabled or disabled on-site by means of software in any desired time intervals and combinations.

Another advantage consists in the possible cost reduction because a universal or general-purpose system is fabricated.

The invention also makes it possible to develop new applications with a basic system (apparatus), where retrofitting or expansion or limitation of the range of functions is carried out on site by the customer not by changing hardware, but only by means of different software; and with existing base systems the marketing of the range of functions which was formerly tied to hardware sales is now made possible exclusively based on software via the Internet for individual examinations and functions within a limited time or very economically for an unlimited time.

The invention represents a transition from the manufacture of many instrument systems to the manufacture of only one instrument system whose application characteristics are no longer determined by manufacture, but by programming only.

The invention will be described more fully in the following based on a number of embodiment examples referring to the drawings.

BRIEF DESCRIPTION OF THE DRAWINGS

In the drawings:

FIG. 1a shows the optical arrangement for a first embodiment example of an apparatus;

FIG. 8c shows an optical arrangement for a tenth embodiment example of an apparatus;

FIG. 10 shows a flowchart for an examination sequence;

FIG. 15 shows beam bundles in the operation of an apparatus as light scanner;

DESCRIPTION OF THE PREFERRED EMBODIMENTS

Figure 1B:
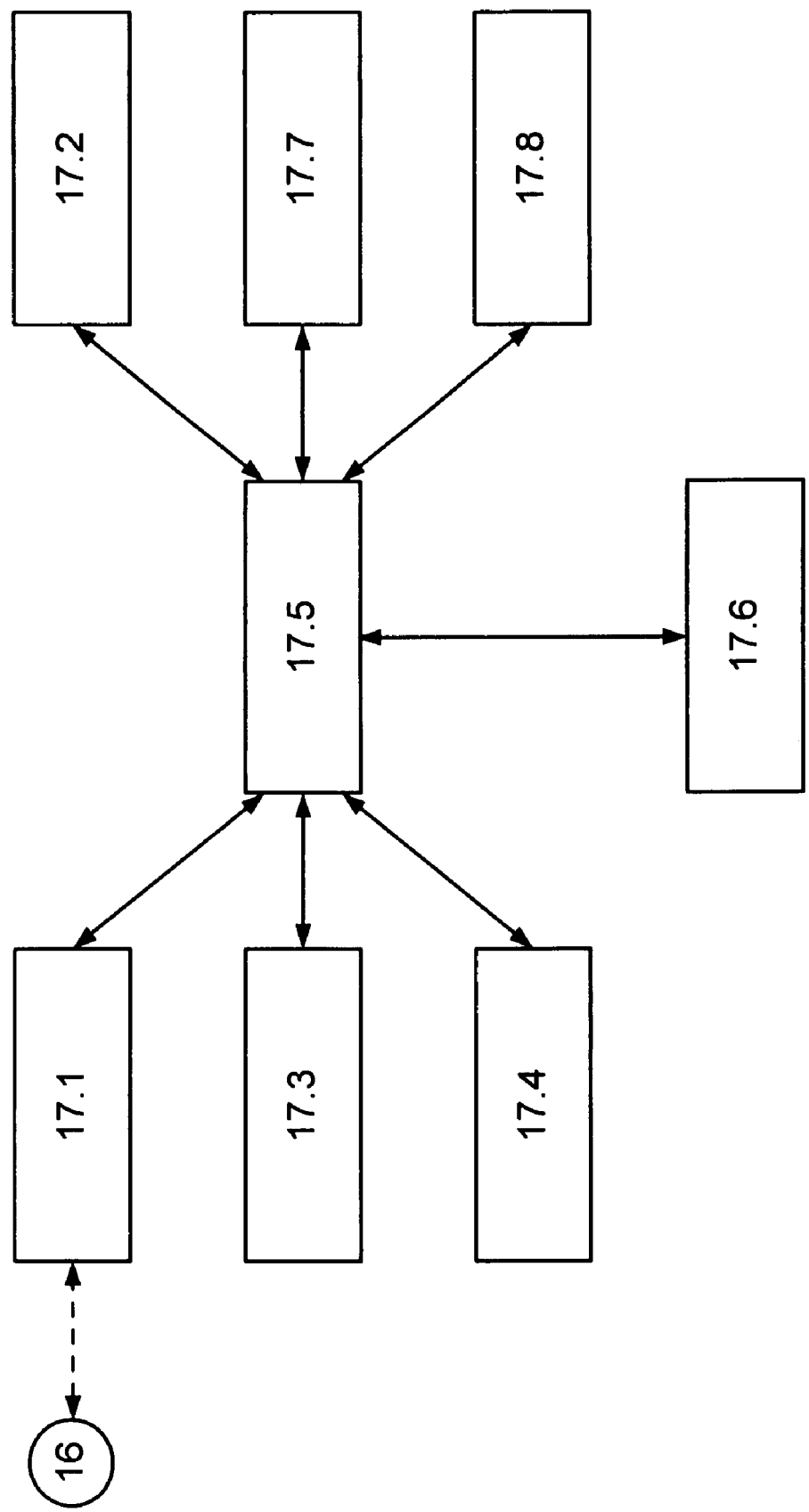
FIG. 1b is a schematic view of an ITS.

The follow embodiment examples characterize the many areas of application of the invention. Embodiment examples for ophthalmology and optometry will be especially emphasized and described particularly thoroughly and may also be applied in a corresponding sense to other areas of application within or apart from medicine. The individual embodiment examples for an apparatus according to the invention differ with respect to instrumentation in the construction of the optical arrangement.

In a first embodiment example, the optical arrangement corresponds to a simple reception system 1 as is shown in FIG. 1a. The object plane 3.1 is imaged in the image plane 3.2 by an optics unit 7.4. By pupil plane of the reception system 5.3 is meant the plane in which the aperture diaphragm of the reception system 1 or its image occurs.

According to the invention, a beam manipulation unit EMS 14 whose elements are controllable independently from one another is arranged in a pupil plane 5.3 and in the image plane 3.2, respectively. The EMS 14 in the pupil plane 5.3 is constructed as an EMS in transmission 14.1, while the EMS 14 in the image plane 3.2 is constructed as EMS as receiver 14.4. Both EMS 14 are connected to an information technology system ITS 17 by interfaces 16.

By EMS 14 is meant in the following generally beam manipulation units with at least one optically accessible surface comprising individual, independently controllable elements which can change the impinging radiation through control of the elements or can convert it into electronic signals. By beam manipulation is meant, in this sense, also conversion of electromagnetic radiation into electronic signals.

An EMS 14 comprises at least one component having elements in a surface which can be arranged so as to be optically accessible in a beam path, these elements of the type mentioned above being individually, independently controllable. Such components can be micromirror arrays, LCD displays and microdisplays in transmission or reflection, as well as color displays or CMOS chips as image sensors which can be used in special cases directly as EMS 14 or can act in an arrangement as EMS 14. For example, an LCD chip in transmission with a polarizer arranged in front of the chip in the direction of light can generate an EMS 14 whose transmission is controllable within the optically active surface for each individual element. Further, EMS in transmission 14.1 or EMS in reflection 14.2 can also be generated from LCD reflection components in an optical arrangement. Micromirror arrays or so-called DLP components or DMD components can possibly be used directly as EMS in reflection 14.2. CMOS image sensors with pixels that can be controlled and read out individually are likewise usable directly as EMS as receivers 14.4. In the following, the pixels will likewise be referred to as elements. Also, components which are constructed as arrays with emitting elements can be used, according to the invention, as EMS in emission 14.3. The manner in which an EMS 14 is generated and the kind of components that are used to generate it are not important as regards the invention and all of the other embodiment examples insofar as they have an optically accessible and optically or optoelectronically active surface with elements which can be controlled individually and independently from one another and which can manipulate the beam in a controllable manner or convert it into electronic signals.

In special cases, it can be advantageous that the EMS 14 comprises one individual element.

An information technology system ITS 17 is shown schematically in FIG. 1b. It comprises control units 17.1 which are connected, via interfaces 16, to the controllable units of the optical arrangement, in this case the EMS 14.1 and EMS 14.4. A central unit 17.5 is connected to data, signal and/or image storage units 17.2, signal and/or image processing units 17.3, evaluating units 17.4, units for conversational mode or dialog operation and for results presentation 17.6, the program library 17.7, and the units for results documentation 17.8.

While the control units 17.1 control the controllable units of the optical arrangement, in this case the EMS 14.1 and 14.4, and convey the data, signals and images retrieved by these units to the information technology units of the ITS, the other units of the ITS serve to implement the method according to the invention which is provided with the apparatus and which will be described more fully in the following.

Figure 1C:
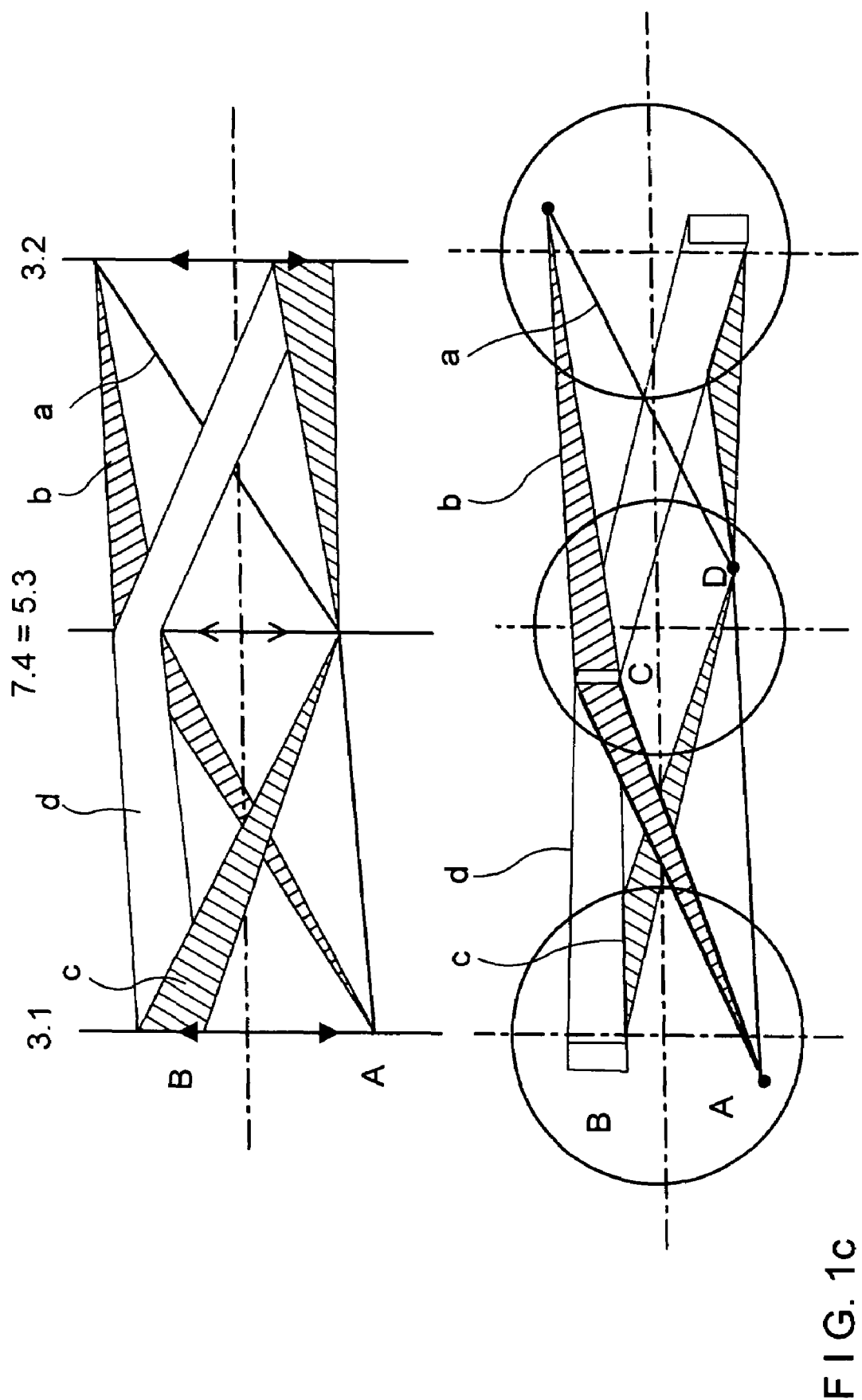
FIG. 1c shows a beam bundle for the first embodiment example.

According to the invention, the characteristics of the described device which define its suitability as an imaging, measuring and/or testing device are now determined solely by programming by means of the method for operating the device. The action of the method according to the invention is described by means of FIG. 1c. FIG. 1c shows possible beam bundles in the optical arrangement from FIG. 1a which can be generated solely through programming of the EMS 14.1 and 14.4. The principal plane of the optics unit 7.4 was situated in the pupil plane 5.3 in order to simplify the illustration.

That control unit 17.1 which controls the elements of the EMS in transmission 14.1 can change the transmission of the individual elements independently from one another. A classic pinhole diaphragm would be implemented as aperture diaphragm of the system if the control were carried out in such a way that a centric circular surface of elements was fully turned on and the rest of the elements were switched so as not to transmit light. The advantage from this perspective would consist already in that different apertures are realized with high accuracy and these apertures are varied over time with a high time resolution. This would mean that changes in illumination, for example, could be compensated during a recording or measuring process by varying the pupil aperture without moving any mechanical part. Further, a large number of apertures of different geometry with any position and surface can now be realized by programming technique and can be varied with a high time resolution. In addition, not only is it possible to switch back and forth between maximum and minimum transmission, but defined transmission values can also be adjusted therebetween. Accordingly, the action of an EMS 14 located in the pupil is no longer comparable to a conventional aperture diaphragm, but rather opens up a completely new area of application that can not be realized by the prior art. Through programming technique, the EMS in transmission 14.1 can determine the transmission and the aperture of an individual elemental beam bundle which is defined only by its element size.

By means of the EMS as receiver 14.4 in the image plane 3.2, which is constructed as a CMOS image receiver with elements that can be read out individually, any surface elements in the image plane 3.2 which are conjugate to the object plane 3.1 and whose information is conveyed selectively to the ITS 17 can be determined by programming without having to read out the entire image. In addition, every element is adjustable differently with respect to its sensitivity. Individually, these advantages of CMOS receiver technology are known prior art.

Due to the combination and the independence of the controllability of all elements of the EMS 14.1 and EMS 14.4, any elemental beam bundles can be generated according to the invention within the framework of the optically active or optoelectronically active element number. By elemental beam bundle is meant the beam bundle between the object point or a conjugate image point and the aperture point in the associated pupil. By point is meant ideally the respective surface of the element or its conjugate image surface. An elemental beam bundle of this kind is obtained when only one element of the EMS 14.1 is turned on and only one element of the EMS 14.4 is read out.

FIG. 1c shows an elemental beam bundle a of the kind mentioned above in the object space and image space. The direction of the elemental beam bundle is determined by the position of the surface elements A and D. When a plurality of contiguous elements of the EMS 14.1 or 14.4 are turned on simultaneously, this results in beam bundles b, c and d, each of which is composed of a plurality of elemental beam bundles. The characteristics of these bundles vary. They differ not only in direction, but also with respect to their aperture and their object-side or image-side surfaces. According to the invention, not only can a plurality of different elemental beam bundles be realized with different directions and different points passing through the pupil plane and object plane or image plane, but any quantity of contiguous beam bundles of different characteristics (geometric shape and surface in the planes of the pupil, object and image) can be generated simultaneously or successively and can be varied in time with high time resolution. Aside from the characteristics already mentioned, additional characteristics can now be allocated independently to each elemental beam bundle. For this embodiment example, the value of any one elemental beam bundle with respect to the overall brightness of the image point can be controlled by way of the transmission of the elements of the EMS 14.1. On the other hand, the sensitivity with which every image point enters the subsequent signal analysis or image analysis can be controlled in turn by the EMS 14.4. Both valuations can be varied with respect to time. For example, according to the invention, by frequency modulation of the individual elements of the pupil, individual elemental beam bundles can be associated through like frequencies with different beam paths which can be separated again from the electronic signal sequences and image sequences based on frequencies by signal analysis, apart from the possibilities for geometrically separating different beam paths through contiguous elemental bundle structures. When different functions are associated with determined beam paths, not only can different image-generating, measuring or testing device systems be generated through programming technique with the simple optical arrangement according to FIG. 1a, but they can also be implemented and carried out simultaneously or in very rapid succession. It will be shown later on how additional degrees of freedom lead to greater variability and multifunctionality through further development of the optical arrangement and how greater adaptivity and learning capability can be achieved for a device solution according to the invention through further development of the method according to the invention.

A large number of imaging, measuring and testing applications can be realized solely through program control in accordance with the first embodiment example described above with one individual manufactured arrangement (FIG. 1a). In addition, the valuations effected by way of transmission and sensitivity enable the detection, measurement and testing of computer operations optically as well as masks for fast acquisition of shapes or changes in shape, transmissions and changes in transmission, changes in color or changes in the position of objects.

The solution according to the invention makes possible adaptive imaging, measurement and testing in medicine and industry.

By means of the solution according to the invention, imaging, measurement or testing can be realized through highly contaminated, reflecting or scattering windows in that the window to the object plane is situated in a plane conjugate to the EMS 14.1. The optimal beam geometry can be adjusted by means of a program algorithm. Changes in transmission in the object space (e.g., examinations in or through flowing liquids) or changes in brightness due to varying illumination conditions or changes in the objects can be determined and eliminated as error sources through corresponding changes in the characteristics of the bundles.

It has already been made clear in connection with this embodiment example that this is no longer a matter of aperture diaphragms in the conventional sense. In addition, since it is possible to conceive of a plurality of EMS 14 in planes which are conjugate to one another, a portion of the elements of the respective EMS 14 can have the character of aperture diaphragms in each of these planes, so that aperture diaphragms acting simultaneously for different object points and image points can be located in different pupil planes. Therefore, no distinction will be made between aperture diaphragms and pupils in the following.

There are additional advantageous developments, application examples and actions according to the invention that are analogous to the application examples described in the following and are explained in more detail in the following.

Figure 2:
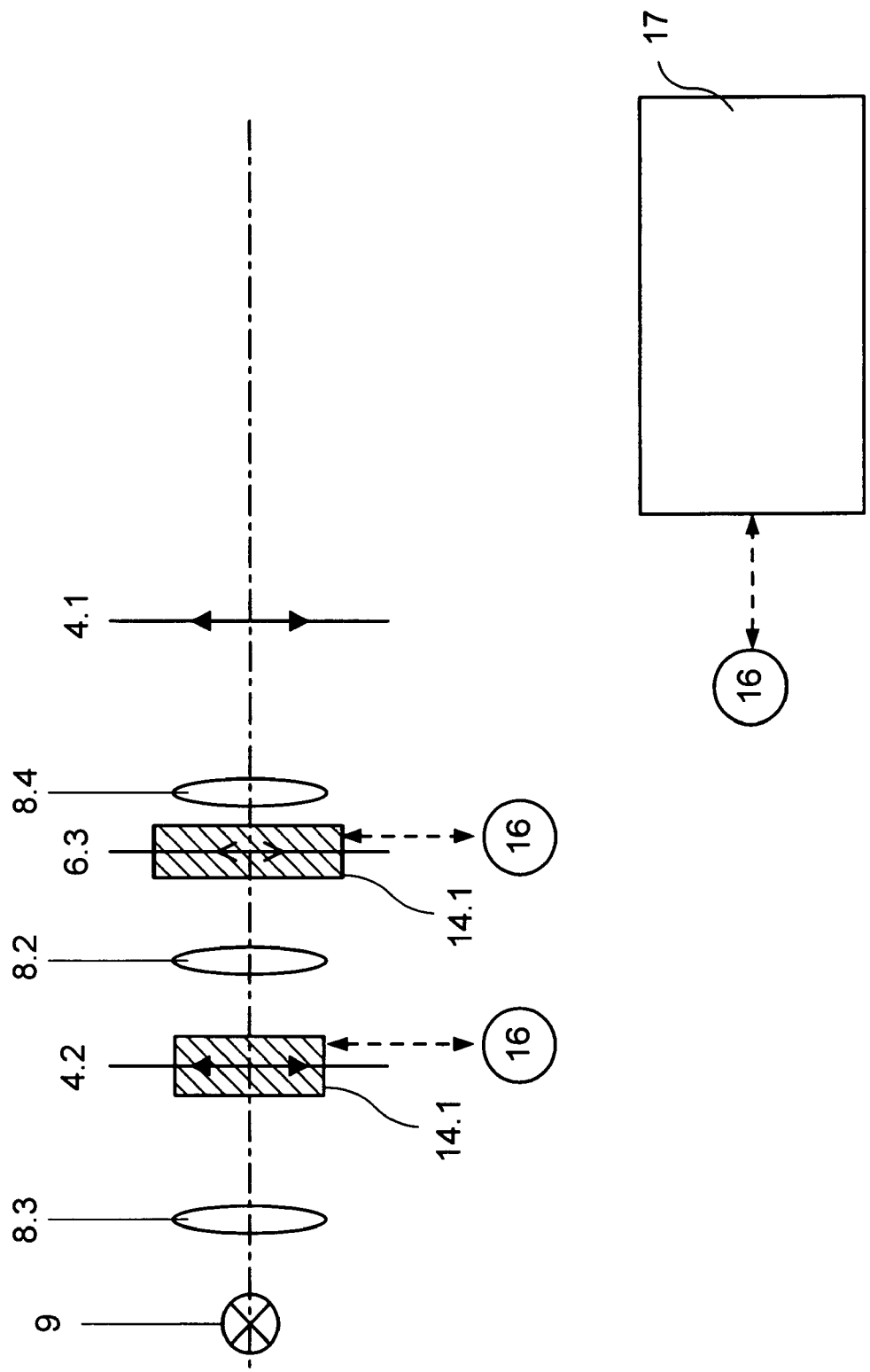
FIG. 2 shows an optical arrangement for a second embodiment example of an apparatus.

In a second embodiment example, the optical arrangement of a device according to the invention corresponds to that of a simple irradiation system 2 shown in FIG. 2. The plane 4.2 in which an EMS in transmission 14.1 is arranged is illuminated by an irradiation source 9 and an optics unit 8.3. Optics unit 8.2, together with optics unit 8.4, images the plane 4.2 in the irradiated plane 4.1 and at the same time generates the pupil plane 6.3 in which another EMS in transmission 14.1 is arranged. The EMS 14 are connected to the ITS 17, described above, by interfaces 16. The schematic view in FIG. 2 shows only the planes that are important for clarification. The two EMS 14.1 are constricted in such a way that their transmission can be controlled independently with respect to the elements in gray scale.

In terms of the function of an irradiation system 2, the irradiated surface 4.1 is decisive. The aperture of the light bundles that is decisive for the points on this surface is determined by the plane 6.3 designated as pupil. Hereinafter and in the following embodiment examples also, all planes conjugate to the plane in which the aperture of the beam bundle which irradiates a point on the irradiated plane 4.1 is determined are designated as pupil planes 5.1 to 5.$n$ and 6.1 to 6.$n$.

Considerations respecting the action according to the invention are analogous to the first embodiment example. The action of the EMS 14.1 in plane 4.2 is sufficiently known from the prior art as used for projectors or from Patent DE 198 12 050 A1. The control of this EMS 14.1 provides a structured illumination in the irradiated surface which can be changed in a variable manner depending upon location and time. However, combining with the EMS 14.1 in the pupil plan 6.3 results in a device system with completely different characteristics. In a manner analogous to the first embodiment example, irradiation-side elemental beam bundles can now be formed and characteristics and, in a further step, functional beam paths can be allocated to these elemental beam bundles as was already described. In particular, by controlling the EMS 14.1 in the pupil plane 6.3 the transmission of every elemental beam bundle can be controlled additionally and independently for the brightness control of the image points through the transmission control of every element in the plane 4.2 conjugate to the irradiated plane 4.1 by means of EMS 14.1. Accordingly, masks can again be generated which can evaluate, correct or compute image structures and, at the same time, pupil structures (the path of the irradiating elemental bundle) independent from one another.

This embodiment example also has broad application possibilities in medicine and industry due to the variable configuration of different beam paths simultaneously or successively by means of programming and the possibility of making different beam paths separable on the reception side, e.g., geometrically or with respect to frequency.

The advantages and applications of the embodiment example are considerably expanded particularly in cooperation with receiver arrangements (see other embodiment examples). Nevertheless, the free programming of the paths of the elemental beam bundles already offers application possibilities for adaptive irradiation-therapeutic and laser-surgical device systems in medicine as well as for industrial adaptive machining of materials, with irradiation through contaminated windows or partially transparent media or for realizing highly precise irradiation energies, local energy distributions or selective irradiation in defined layers of a thick transparent or partially transparent object. Accordingly, transmission differences between different beam paths, for example, can be eliminated as an error source in the generation of uniformly irradiated surfaces.

There are additional advantageous developments, application examples and actions according to the invention that are analogous to the application examples described in the following and are explained in more detail in the following.

Figure 3:
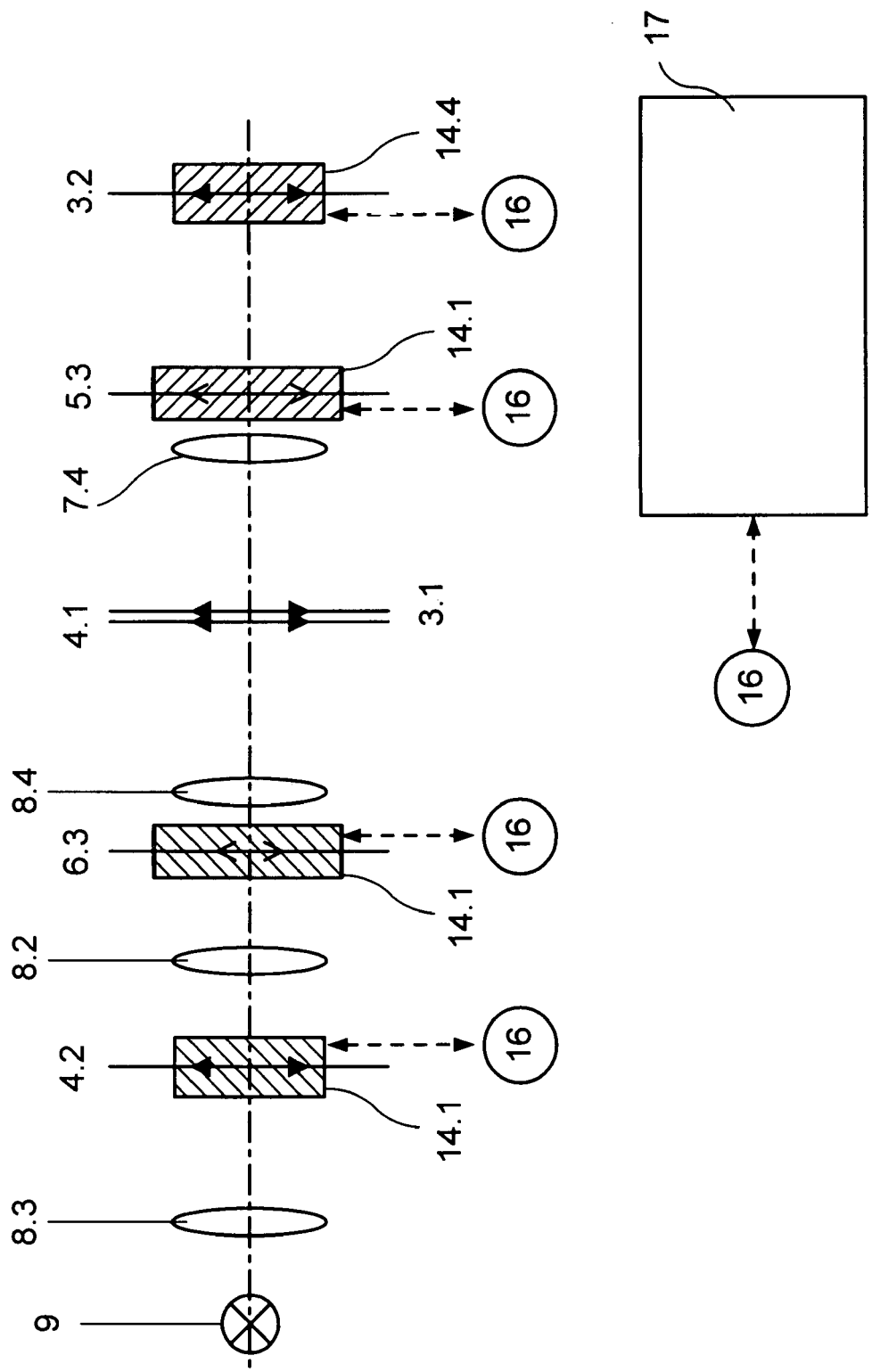
FIG. 3 shows an optical arrangement for a third embodiment example of an apparatus.

FIG. 3 is a schematic view of a third embodiment example which combines the optical arrangements of the first and second embodiment examples. The irradiated plane 4.1 of the irradiation system 2 should preferably be identical to the object plane 3.1 of the reception system 1. The irradiation system 2 should be arranged in transmitted illumination relative to the reception system 1, and arrangements with any angle between the irradiation system and reception system 1 and 2 can be equally advantageous and can be realized simply by means of corresponding mechanical devices. The EMS 14 are again connected to the ITS 17 by interfaces 16.

The multiplicity of application examples and advantages of this arrangement for industrial and medical purposes result from combining the first and second embodiment examples and will be explained more fully with reference to the following embodiment examples.

Four EMS 14 are arranged in this third embodiment example. With two EMS in the total system, e.g., with two EMS in the irradiation system 2 or two EMS in the reception system 1, essential parts of the described actions according to the invention can already be achieved. The use of additional EMS 14 only increases the leeway for imaging, measuring, testing, machining or therapeutic device systems which can be realized in different ways. The cooperation of different EMS 14 and expanded beam paths is likewise described thoroughly with reference to the following embodiment examples for ophthalmological device systems and can be applied in an analogous sense to application areas in medicine outside of ophthalmology and in industry.

Figure 4:
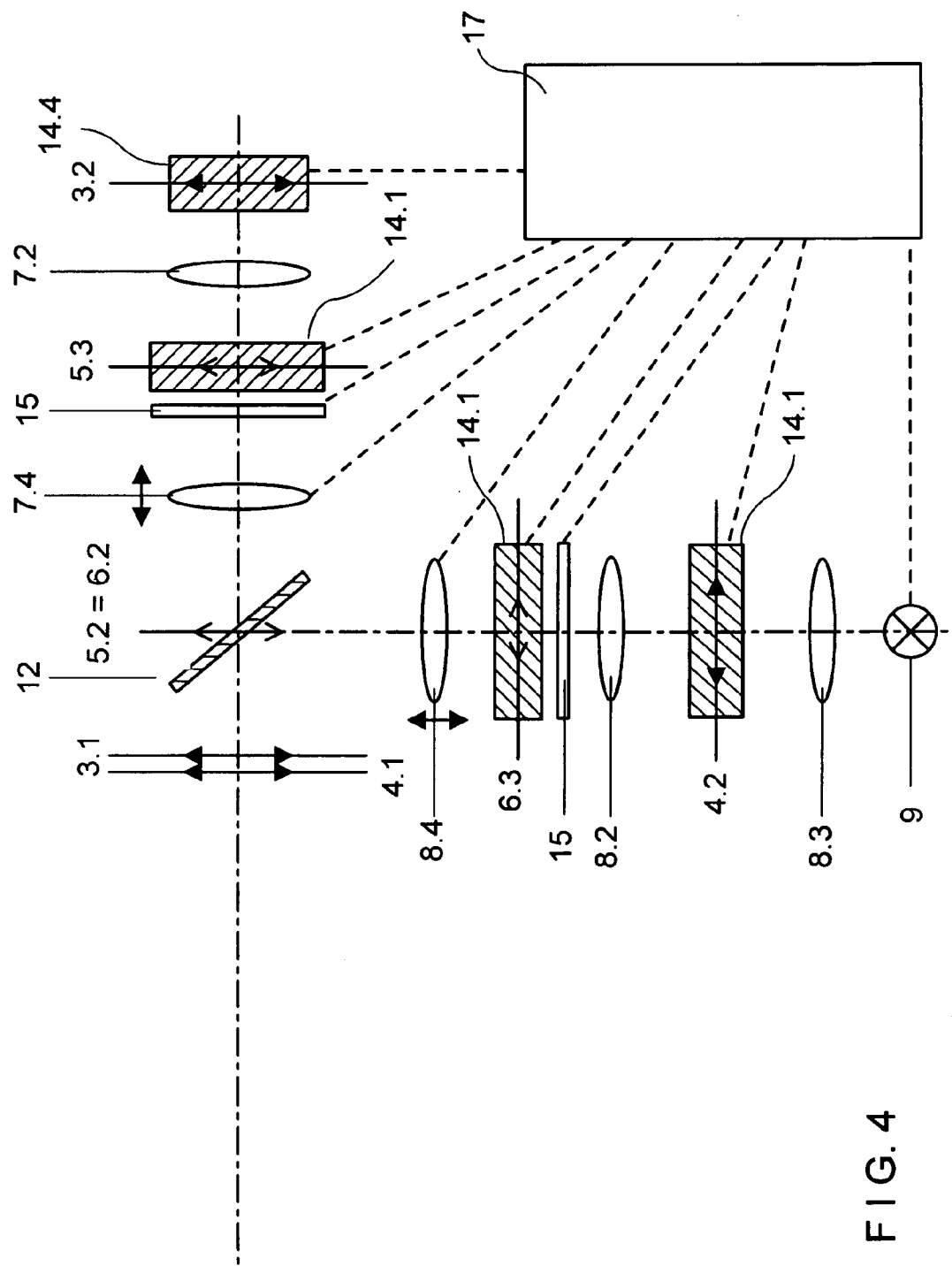
FIG. 4 shows an optical arrangement for a fourth embodiment example of an apparatus.

A fourth embodiment example is shown schematically in FIG. 4. In contrast to the system described in the second embodiment example, the irradiation system 2 is supplemented by a beam splitter 12 which combines the reception system 1 with the irradiation system 2. An additional controllable beam manipulator SM 15 is preferably arranged in the immediate vicinity of the pupil plane 6.3. The pupil plane 6.3 is imaged in pupil plane 6.2. The reception system 1 is arranged in a manner similar to the first embodiment example. The optics unit 7.4 together with optics unit 7.2 images the object plane 3.1 in the image plane 3.2 in which the EMS as receiver 14.4, already described, is located as image sensor. The EMS in transmission 14.1 in the pupil plane 5.3 is imaged through the optics unit 7.4 in the pupil plane 5.2. Another SM 15 is arranged in the immediate vicinity of the pupil plane 5.3. Both systems are combined and constructed in such a way that the pupil planes of the two systems are preferably conjugate to one another and the plane of the irradiated surface 4.1 and the object plane 3.1 fall in a common plane by means of the adjustment of controllable optics units 8.4 and 7.4. All controllable units, including the EMS 14, are connected to the ITS 17, already described, by interfaces 16. The interfaces 16 are shown by dashed lines in FIG. 4.

The SM 15 are constructed as filter wheels having corresponding filters for color examinations or fluorescence examinations.

This embodiment example is preferably used for examining tissue or material in incident or reflected light. Application examples are instruments for imaging, measuring, testing and treatment on and in living and dead tissue, particularly the skin and body cavities. It differs in principle from the ophthalmological embodiment examples presented in the following only in that the irradiated surface and the object surface are situated at infinity. All of the preceding and following descriptions and possible modifications also apply to this apparatus, including the actions and effects according to the invention.

Compared to conventional instruments of this type, advantages consist in the high-contrast images of the objects, multifunctionality, simultaneity of different examinations and in the implementation of adaptivity similar to instruments for examining the eye 10. The many applications and advantages according to the invention as well as the advantageous constructions are identical to or analogous to the following embodiment examples.

Figure 5:
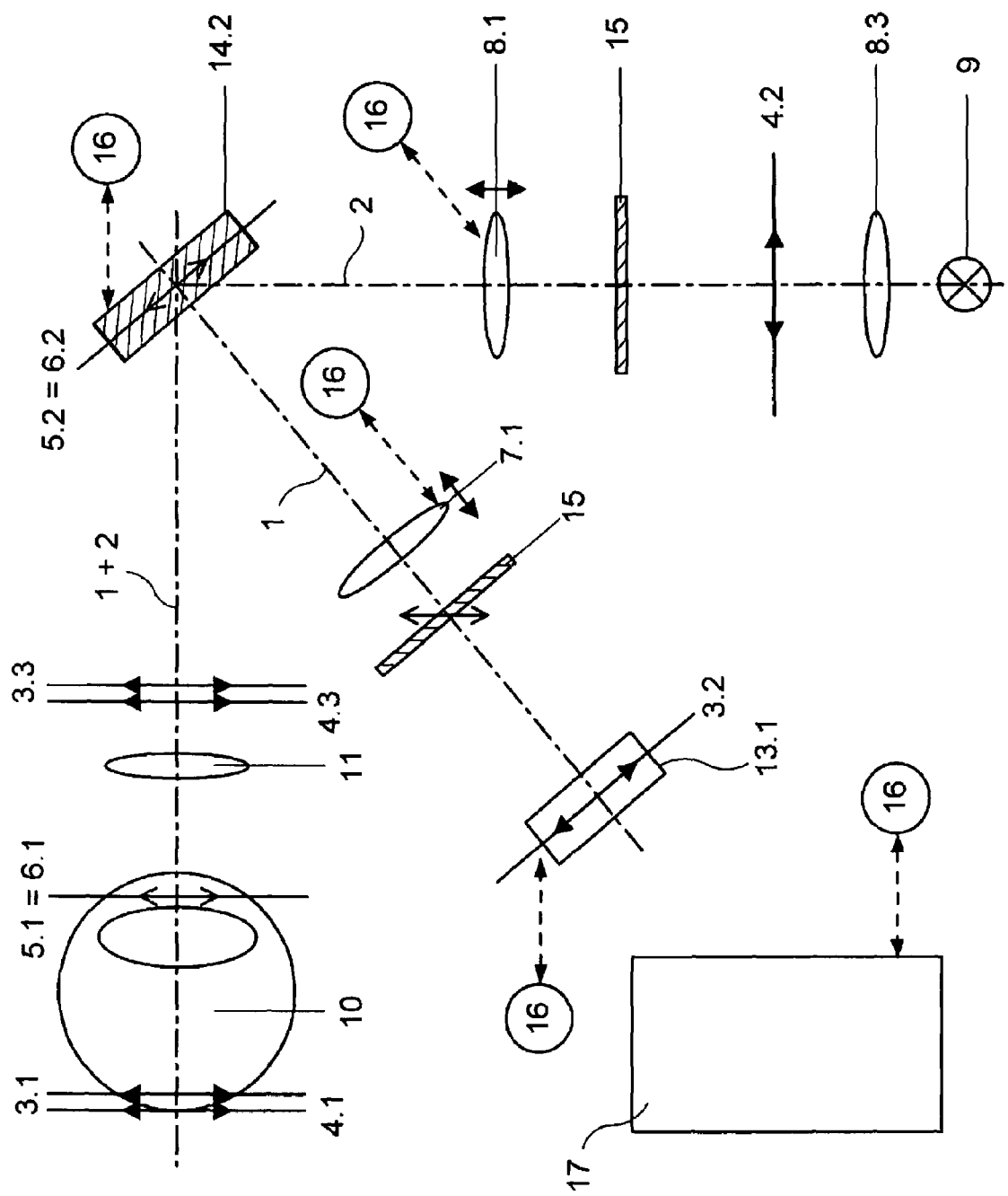
FIG. 5 shows an optical arrangement for a fifth embodiment example of an apparatus.

FIG. 5 shows a fifth embodiment example, an ophthalmological examination device, preferably for objects at the fundus of the eye, based on indirect ophthalmoscopy or retinal camera technique.

As in the preceding drawings, only the planes and units essential to operation are shown schematically.

The optical arrangement of this embodiment example comprises an irradiation system 2 and a reception system 1. The irradiation system 2 irradiates an irradiated plane 4.1 in the eye 10 and the reception system 1 images an object plane 3.1 in the eye 10 in an image plane 3.2. For standard applications, these planes coincide, but this is not necessary. Proceeding from these planes, the irradiation system and reception system 1 and 2 run together through the eye 10, through the pupil of the eye via the ophthalmoscope lens 11, form the intermediate images 3.3 and 4.3 which are conjugate to planes 3.1 and 4.1 and are separated from one another by an EMS 14. Irradiation system and reception system 1 and 2 are arranged in such a way that in a known manner the pupil planes of the two systems 5.2 and 6.2 are conjugate to one another and are imaged one inside the other (5.2=6.2) and are also imaged via the ophthalmoscope lens 11 at the same time in the plane of the pupil of the eye (5.1=6.1). The optically active surface of the EMS 14 is situated in this common pupil plane (5.2=6.2). An EMS in reflection 14.2 based on a mirror array with at least two, but preferably three, defined deflection angles is used in the present embodiment example for beam splitting.

The irradiation system 2 comprises an irradiation source 9 which irradiates a plane 4.2 conjugate to the irradiated plane 4.1 via an optics unit 8.3, an SM 15, an optics unit 8.1 which images the plane 4.2 together with the ophthalmoscope lens 11 and the imaging layers of the eye 10 in the irradiated plane 4.1 via reflecting elements of the EMS in reflection 14.2.

The reception system 1 forms the object plane 3.1 in the eye 10 via the imaging layers of the eye 10, via the ophthalmoscope lens 11, via reflecting elements of the EMS in reflection 14.2, via optics unit 7.1, via an SM 15 in the receiver plane 3.2 in which the image-recording surface of a CCD receiver 13.1 is arranged.

The EMS in reflection 14.2 and all of the other controllable units of the device system 7.1, 8.1, 13.1 and 15 are connected to an ITS 17 via interfaces 16.

The ITS 17 corresponds to the embodiment form which was already described. The units for results documentation 17.8 are constructed as units for the patient-related database and for the patient data and image management. Further, the units for dialog operation and for results presentation 17.6 are expanded by units for information exchange with networks particularly with the WWW.

The optics units 7.1 and 8.1 which are shown schematically serve to focus the irradiated plane 4.1 and the object plane 3.1 in the desired plane in the eye 10 and for compensation of defective vision without changing the position of the pupil planes. The SM 15 are constructed as controllable filter wheels for color fluorescence, autofluorescence and examinations with fluorescence indicators.

According to the invention, the action of the pupils of the illumination beam paths and reception beam paths and the beam splitting is freely programmable by means of controlling the EMS in transmission 14.1. As was already described, elemental bundles are formed between each point on the planes 4.1 and 3.1 and each element of the mirror array of the EMS 14 by the independently controllable elements of the EMS 14. Corresponding to the method according to the invention, these elemental beam bundles are associated with or reflected out of the irradiation system or reception system 2 and 1 by controlling the mirror elements of the EMS in reflection 14.2. The reflecting out is effected for generating a beam-free space. Further, the number or surface of the elements associated in each instance with a system determines the effective aperture and, accordingly, essential characteristics for imaging, measuring, testing, stimulating or treating the eye 10. Due to the position, geometric shape and surface of the mirror elements in the pupil plane which are connected to form a system, the intensity, wave-optical, spherical and chromatic imaging errors, astigmatism, geometric resolving power, photometric resolution and detection limit, and the proportion of interfering reflected light or scattered light are determined among others. With the apparatus and method according to the invention, depending on the high individual variability of the eye of the patient and the goal of an examination, it is possible to find an optimal compromise between these characteristics and to adapt the solution respecting instrumentation and its system parameters individually to the examination and to the given factors of the individual eye 10. These characteristics of the invention are referred to as functional adaptivity and individual adaptivity. According to the method, optimization programs which determine the optimal adjustments while taking into account the goals of examination and distinctive features of the patient are carried out. In addition to this, as was already described, characteristics such as allocation to the irradiation system or reception system 2 and 1, or reflecting out, the path of the elemental beam bundles through the ocular media, volume of beam-free space, and position of the pupil surface in the iris are associated with the possible elemental beam bundles by programming through control of EMS 14 as are the spectra for color examinations or fluorescence examinations and the position of the planes 3.1 and 4.1 in the eye 10 by controlling the other controllable units. This results in the functional beam paths of the irradiation system and imaging system for illumination and for imaging in the device system and in the eye 10. As was described before, with the high time resolution of the EMS 14, additional characteristics can be associated with elemental beam bundles by means of time modulation (e.g., frequency modulation or time succession) and accordingly other different beam paths are formed from elemental beam bundles with the same characteristics whose different information can be split again by signal analysis or image analysis as was already described.

In contrast to this, the characteristics of the prior art solution regarding instrumentation by means of pinhole mirrors and antireflection diaphragms determined by manufacture is fixed and not adaptable.

Other actions according to the invention are achieved when the embodiment example is modified in that the EMS 14 is constructed as EMS in transmission 14.1 and is arranged in the plane 4.2 in the irradiation system 2 conjugate to the irradiated plane 4.1 or the EMS 14 is constructed as EMS as receiver 14.4 and is arranged in place of the CCD receiver 13.1.

With an EMS in transmission 14.1 in the plane 4.2, different beam paths with completely different functions can be generated by means of the independent control of different transmission values of the elements of the EMS 14 corresponding to the method according to the invention, which functions far exceed the fields of application of a retinal camera as will be shown in the following in an embodiment example relating to the method according to the invention.

Again, programmed characteristics such as position, color, modulation frequency or runtime performance and transmission values are associated with the elemental beam bundles which are formed in this case between the mechanical apertures of the diaphragms in the pupil planes and the elements of the EMS 14 or their images, and a plurality of beam paths can be generated simultaneously or in rapid succession by means of identical characteristics, particularly as was already described, by timed association or frequency characteristics. An example is the simultaneous generation of a fixation beam path, an imaging or documentation beam path, a measurement beam path and a stimulation beam path as will be described below. Since solutions of this kind, according to the invention, can be arranged in a substantially more advantageous manner with the following embodiment examples, reference is had to the following remarks which are to be applied to these simple embodiment examples in an analogous manner.

Figure 6:
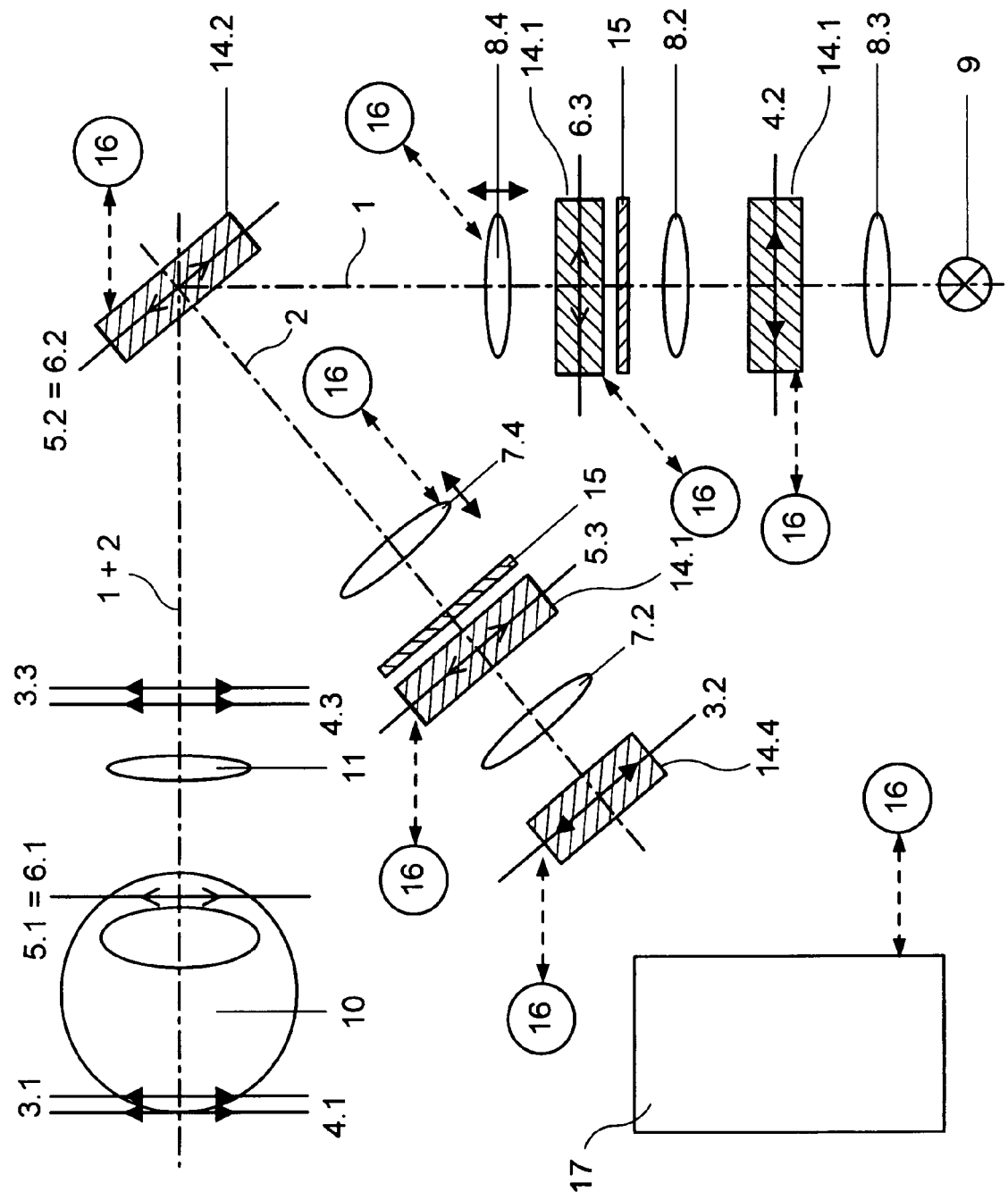
FIG. 6 shows an optical arrangement for a sixth embodiment example of an apparatus.

FIG. 6 shows a sixth embodiment example, likewise an ophthalmologic instrument, preferably for the fundus of the eye. The optical arrangement shown in this case differs from the preceding embodiment example in that additional EMS 14 are provided. In the irradiation beam path, the optics unit 8.1 is replaced by units 8.2 and 8.4 which, above all, generate another pupil plane 6.3 conjugate to pupil plane 6.2 in which another EMS in transmission 14.1 is arranged. A third EMS 14 is constructed in transmission and is arranged in the plane 4.2 conjugate to the irradiated plane 4.1. In the reception system 1, the CCD receiver 13.1 is replaced by an EMS as receiver 14.4 and the optics unit 7.1 is replaced by two optics units 7.2 and 7.4 so that an additional pupil plane 5.3 conjugate to 5.2 is generated. Another EMS in transmission 14.1 is arranged in this pupil plane 5.3. All other EMS 14 as well as the controllable optics units 7.4 and 8.4 are connected to the ITS 17, already described, by interfaces 16. The controllable optics units 7.4 and 8.4 can implement focusing in the desired position in the eye 10 for the object plane and the irradiated plane in connection with compensation of defective vision. In addition, these units can adjust the imaging scale preferably continuously. These adjusting functions leave the position of the pupil plane 5.2 or 6.2 unchanged.

As in the fifth embodiment example, the beam splitter 12 is constructed in the pupil plane 5.2=6.2 as EMS 14 based on a mirror array whose inventive action has already been described. The additional EMS 14 considerably expand the advantages of the invention. According to the invention, any independent elemental beam bundles such as those already described in the third embodiment example can now be generated in the reception system as well as in the irradiation system. These elemental beam bundles are generated by controlling the elements of the EMS 14 and are formed between the elements of the image planes and associated pupil planes insofar as these elements allow radiation which is effective with respect to reception and irradiation. In addition, any elemental beams can be associated with the reception or observation system 1 with the beam splitter 12 as EMS 14.

The EMS in reflection 14.2 does not need three deflecting angles to reflect out beams because the EMS in transmission 14.1 of the pupil planes are conjugate to the EMS in reflection 14.2. This function can be realized by means of controlling the EMS 14 in the pupil planes 6.3 and 5.3 in that these EMS in transmission 14.1 limit the beam bundles and accordingly any beam-free space between the reception-side and radiation-side bundles can be generated for eliminating reflected light and scattered light.

At the same time, interfering beam bundles can be eliminated with the EMS 14 in the pupil plane 6.3 in that the transmission of the corresponding elements is switched off.

Another action of EMS 14 in conjugate arrangement relative to one another consists in that an increase in contrast can be achieved in the irradiated plane 4.1 and in the receiver plane, e.g., by multiplication of the transmission values to the elemental beam bundles and, in addition, computer operations, e.g., for correcting illumination ratios or large differences in reflection or remission in the object plane area (example: foveola and optic disk) in addition to the generation of different beam paths.

Another advantage according to the invention for the EMS in reflection 14.2 as beam splitter between the irradiation system and reception system 2 and 1 results when the mirror tilting is continuously controllable in a sensitive manner in addition to the defined angular position, since in this case wavefront corrections can also be achieved for increasing the imaging resolution.

Figure 7:
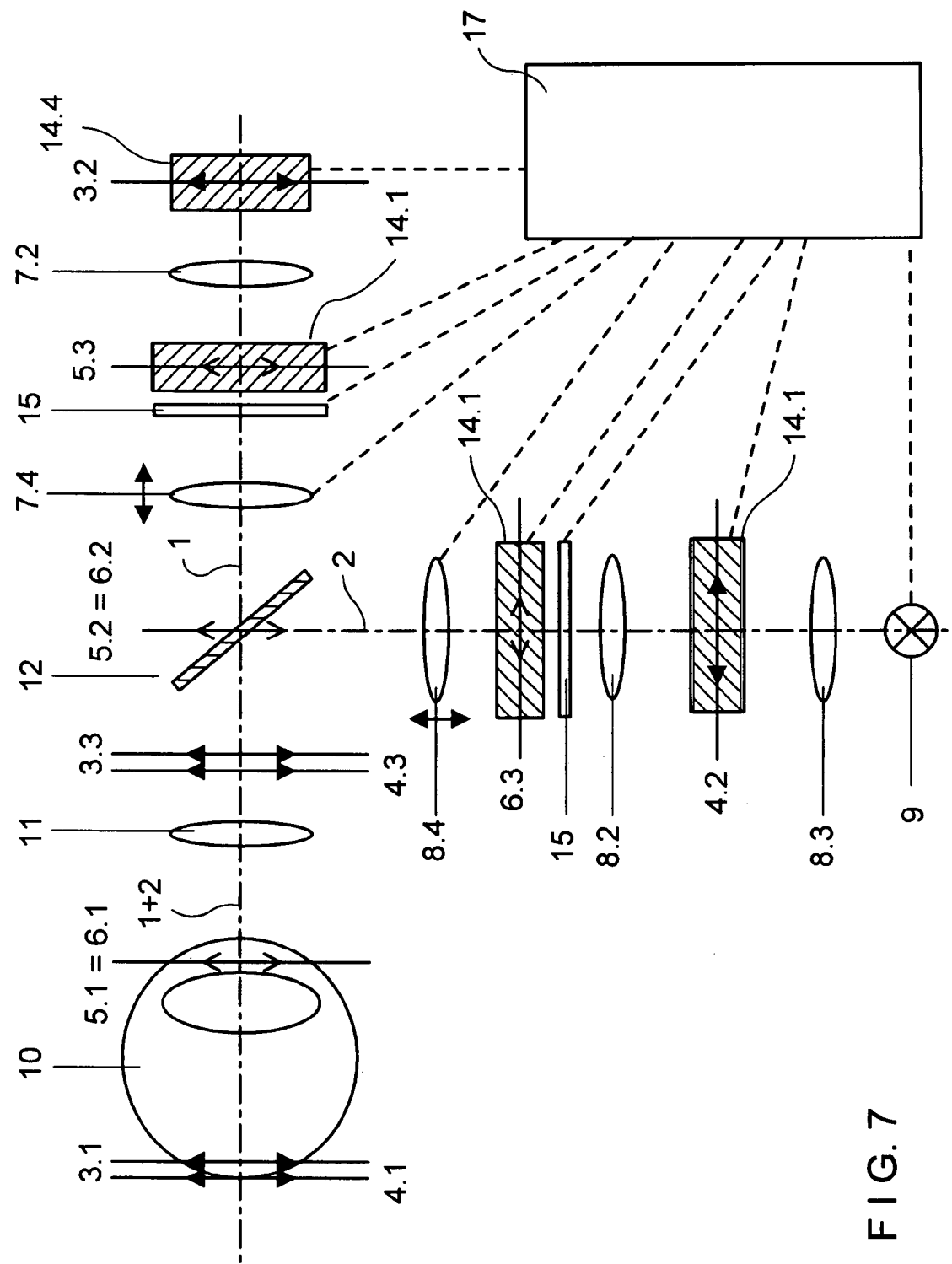
FIG. 7 shows an optical arrangement for a seventh embodiment example of an apparatus.

FIG. 7 shows a seventh embodiment example which differs from the sixth embodiment example only as regards the separation of the irradiation system and reception system 2 and 1. A partially transparent beam splitter 12 is arranged instead of the EMS 14 or the conventional pinhole mirror and need no longer be situated compulsorily in the common pupil plane 5.2=6.2. The interfaces 16 which connect the controllable units of the irradiation system and reception system 2 and 1 to the ITS 17 are shown as dashed lines in FIG. 7.

In contrast to an EMS 14 whose elements associate the elemental beam bundle with the irradiation and reception system 2 and 1 only incompletely and therefore do not enable a coincidence of the pupil apertures of both systems, an optional coincidence of the pupil apertures of the two system can be realized with the solution suggested in this example by means of partially transparent beam splitters 12. This can be particularly advantageous when the absence of reflection can be realized by spectral beam splitting, for example, but not by geometric beam splitting. This is the case, for example, in fluorescence examinations. While the exciter wavelength is adjusted in the irradiation system 2 by means of SM 15, the exciter wavelength is blocked in the reception system 1 by means of SM 15 and only the fluorescence wavelength is permitted. Of course, geometric beam splitting can also be realized by means of EMS 14 of the pupil planes. For the suggested solution from FIG. 7, the conventional pinhole mirror can also be used as beam splitter 12 for splitting reception system and irradiation system 1 and 2. In this case, the possible usable areas of the pupil plane for the formation of elemental beam bundles in both systems would be strictly limited by the conventional pinhole mirror, but would remain freely programmable in the pupil areas which are fixedly predetermined for the irradiation or reception system 2 and 1. The use of a pinhole mirror would accordingly limit the possible freely programmable characteristics.

Further actions and advantages which can be achieved in connection with the method according to the invention are shown in detail with the description of the embodiment examples for the methods according to the invention which will be described subsequently.

The embodiment examples 1 to 7 described herein can be further modified to increase the degrees of freedom for the functionality of the programmable elemental beam bundles or beam paths.

Figure 8A:
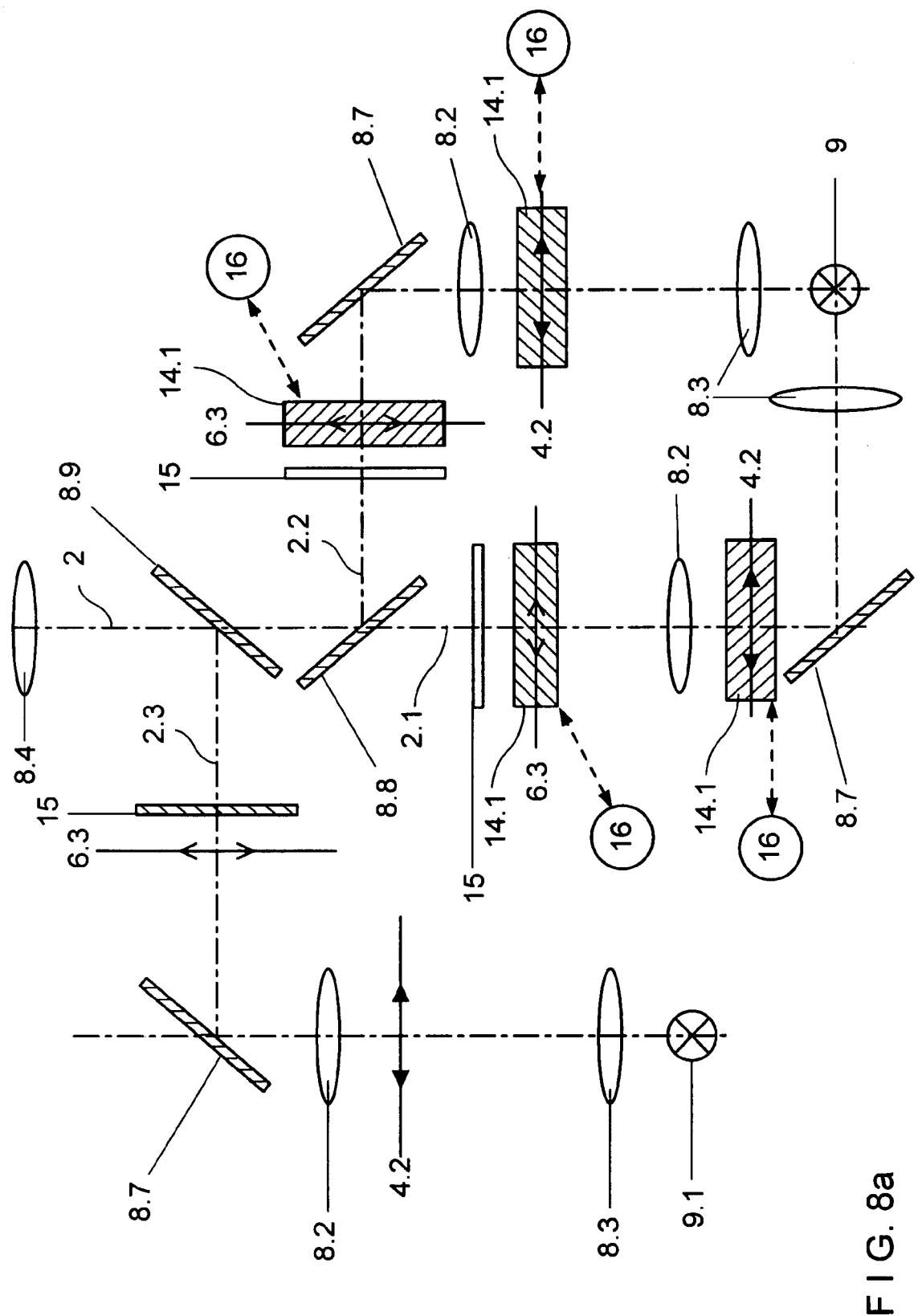
FIG. 8a shows an optical arrangement for an eighth embodiment example of an apparatus.

FIG. 8a shows an advantageous eighth embodiment example for an irradiation system 2 with two parallel, nearly identical partial systems 2.1 and 2.2 and another partial system 2.3.

The third partial system realizes a parallel infrared illumination of the irradiated plane 4.1 which is required by a reception-side partial system, to be described in the following, for recording infrared images. For this purpose, an infrared source 9.1 is fed, via optics units 8.3 and 8.2 and by means of a deflecting mirror 8.7, to a spectral splitter which mirrors the infrared radiation into the common irradiation beam path. This partial beam path can be spectrally tuned by means of the SM 15.

The infrared image recording is preferably realized on the irradiation side and reception side via a separate partial system, since the recording of infrared images and the evaluation thereof by means of a successor program represents a possible solution for the detection and correction of eye movements which is useful in most examinations.

The irradiation system 2 comprising portions 2 and 2.1 or 2 and 2.2 corresponds with respect to function to the irradiation system 2 from FIGS. 6 and 7 and need not be described again. The portion of the irradiation system 2 in FIG. 6 and FIG. 7 from the irradiation source 9 up to and including the SM 15 was constructed a second time and integrated into the irradiation system 2 parallel to one another as partial system 2.1 and 2.2. The irradiation source 9 is used by both partial systems. The deflecting mirrors 8.7 serve for deflection and the combination of the partial systems 2.1 and 2.2 is carried out by means of the partially transparent mirror 8.8.

The action of a partial system with an EMS in transmission 14.1 in the irradiated plane 4.1 and an EMS in transmission 14.1 in a pupil plane was already adequately described. By means of the arrangement of two parallel partial systems of this type, the irradiation-side elemental beam bundles which are freely programmable independent from one another in every partial system are provided with another independent characteristic, e.g., a different spectral characteristic, and overlap one another. As was already described, the spectral characteristic can be carried out by the EMS 14 as the construction of a controllable filter wheel, but also as a controllable spectrally tunable filter. The result is increased degrees of freedom for the programmable characteristics and functionality of the solutions according to the invention.

Figure 8B:
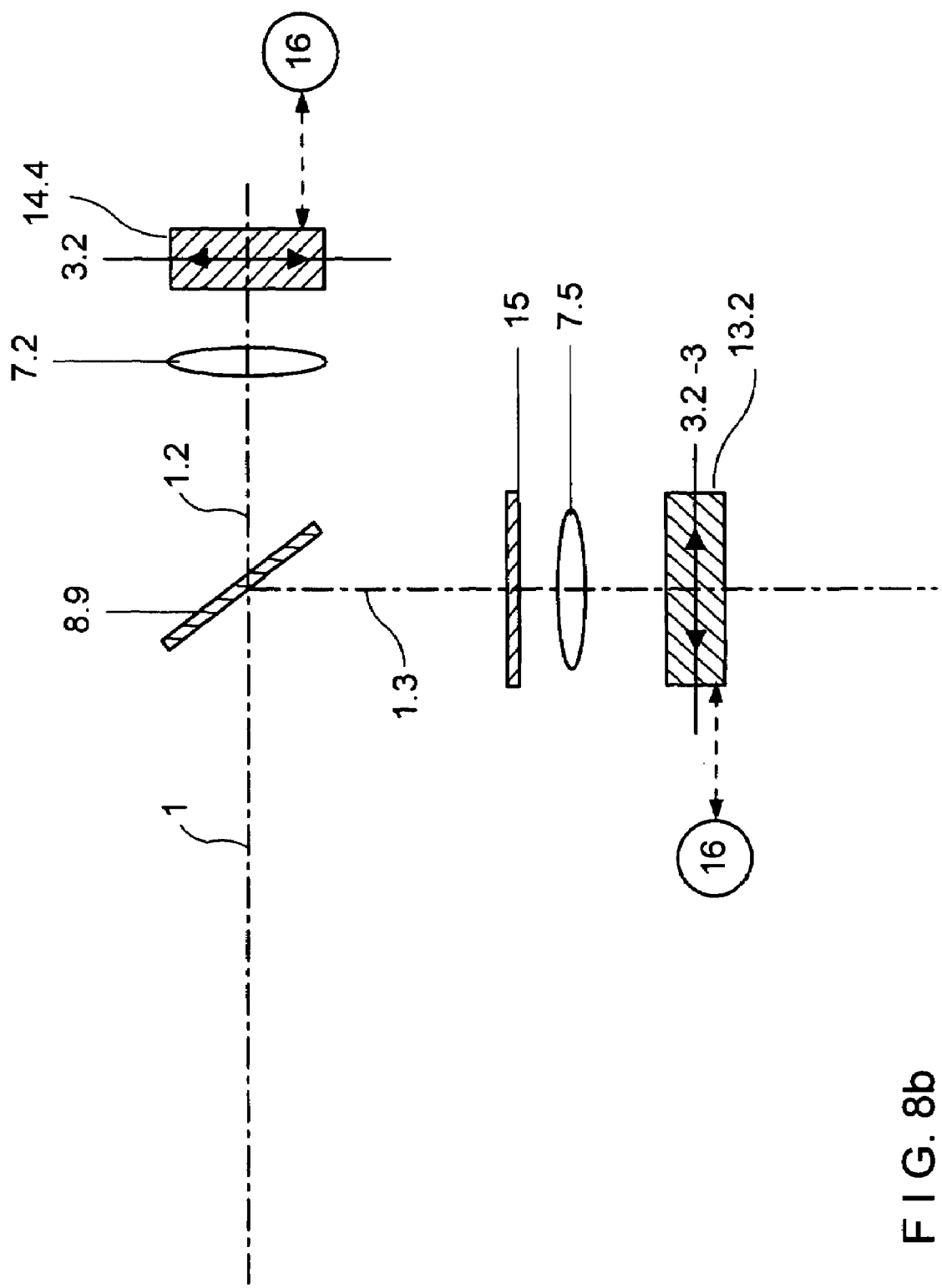
FIG. 8b shows an optical arrangement for a ninth embodiment example of an apparatus.

A ninth embodiment example is shown in FIG. 8b. For recording infrared images, a spectral splitter 8.9 which deflects the infrared radiation into a reception-side partial system 1.3 is introduced into the reception system 1. The optics unit 7.5 images the object planes 3.1 on an infrared image receiver 13.2.

A tenth embodiment example shown in FIG. 8c is another solution according to the invention for the advantageous generation of partial systems using the example of the reception system 1. For example, when the EMS 14 of the pupil plane of the reception system 1 of embodiment examples 6 and 7 is constructed not as EMS in transmission 14.1, but as an EMS in reflection 14.2, e.g., based on a mirror array with at least two defined deflecting angles, the reception system 1 can be divided into two partial systems 1.1 and 1.2. A second EMS as receiver 14.4 should preferably be arranged in the image plane 3.2 of the second partial system 14.2 conjugate to the object plane 3.1. The partial system 1.2 is constructed analogous to the partial system 1.1. The apparatus and action of the irradiation system 2 along the partial system 1.1 was already described in the sixth and seventh embodiment examples and applies in an analogous manner also to partial system 1.2.

The advantageous action of this arrangement consists, e.g., in that it can be decided solely by means of programmed control of the EMS in reflection 14.2 in the pupil plane whether or not the EMS as receiver 14.4 supplies, e.g., stereo images or, e.g., spectrally differing images from the same angle of observation. When the elements of the EMS in reflection 14.2 are controlled in such a way that a geometric pupil division is carried out, i.e., half of the respective adjacent elemental beam bundle is associated with partial system 1.1 as assigned bundle, while the other half is associated with partial system 1.2, stereo images are obtained. When the elements are controlled in such a way that the elemental beam bundles are associated alternately with partial system 1.1 and partial system 1.2, this approximates the effect of amplitude splitting. In the latter case, the two partial systems 1.1 and 1.2 can be spectrally tuned differently by means of SM 15, while the SM 15 should advantageously have the same effect in both partial systems 1.1 and 1.2 in case of stereo operation.

Figure 9A:
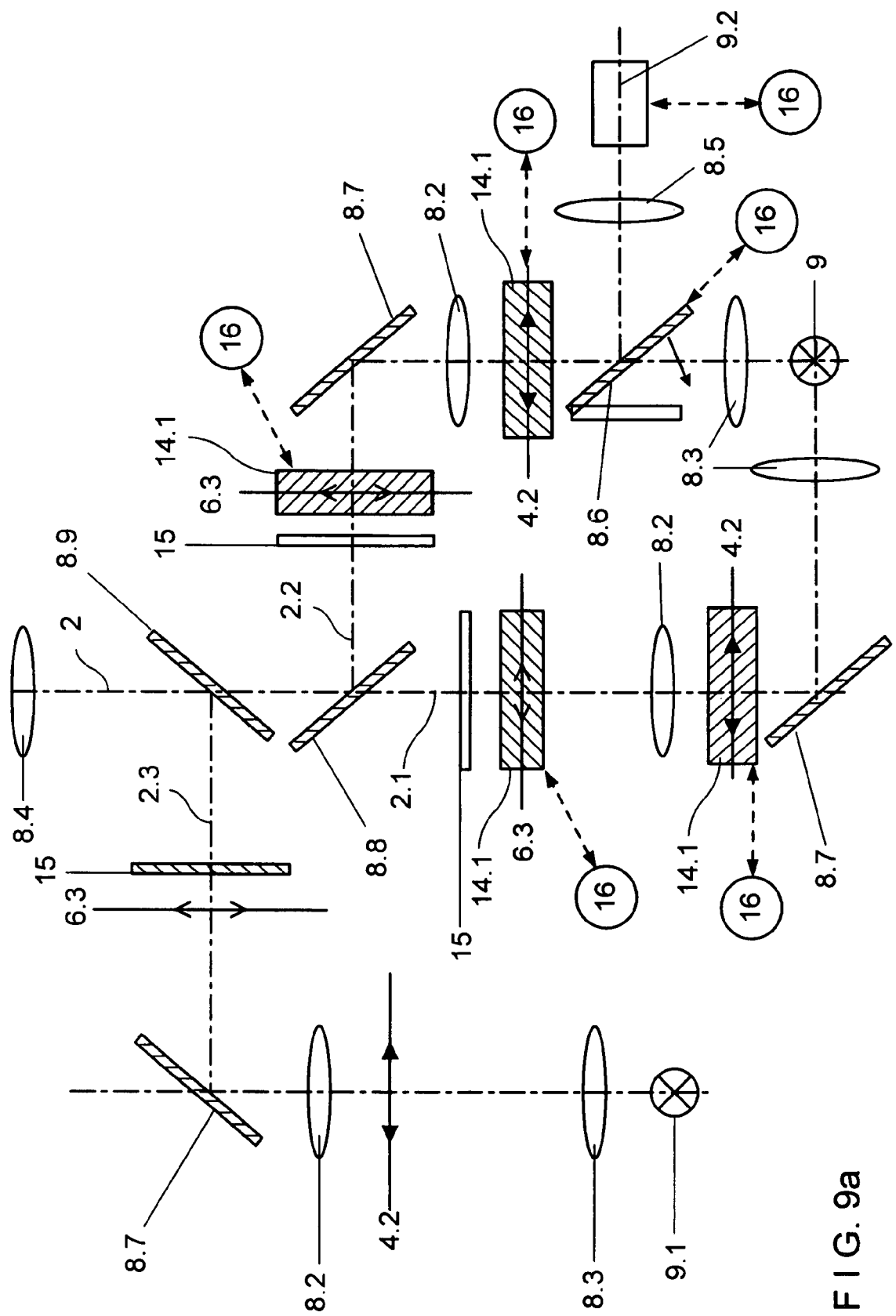
FIG. 9a shows an optical arrangement for an eleventh embodiment example of an apparatus.

An eleventh embodiment example is explained with reference to FIG. 9a. The eighth embodiment example shown in FIG. 8a is modified in that it is supplemented by a therapy beam path, for example, for photodynamic therapy on the eye 10 for treating AMD. A corresponding AMD-capable and controllable therapy laser 9.2 is mirrored into the beam path of the partial system 2.2 when required via an optics unit 8.5 and a controllable swing-out mirror 8.6. Swing-out mirror 8.6 and therapy laser 9.2 are connected to the ITS 17 by interfaces 16. The optics unit 8.5 provides for an illumination of the EMS in transmission 14.1 in plane 4.2 with the laser light. Corresponding to the action already described, therapeutic elemental beam bundles can now be formed which can form any desired geometric shape in the irradiated plane 4.1 with any intensity patterns, while additional beam paths for other functions can be generated by programming via the partial system 2.2 simultaneous with the therapy. A first clear advantage consists in that the therapy system is combined with the examination system in one device. The graphic examination results, which are currently obtained by image evaluation of the fluorescence of angiographic images are immediately available for therapy.

Figure 9B:
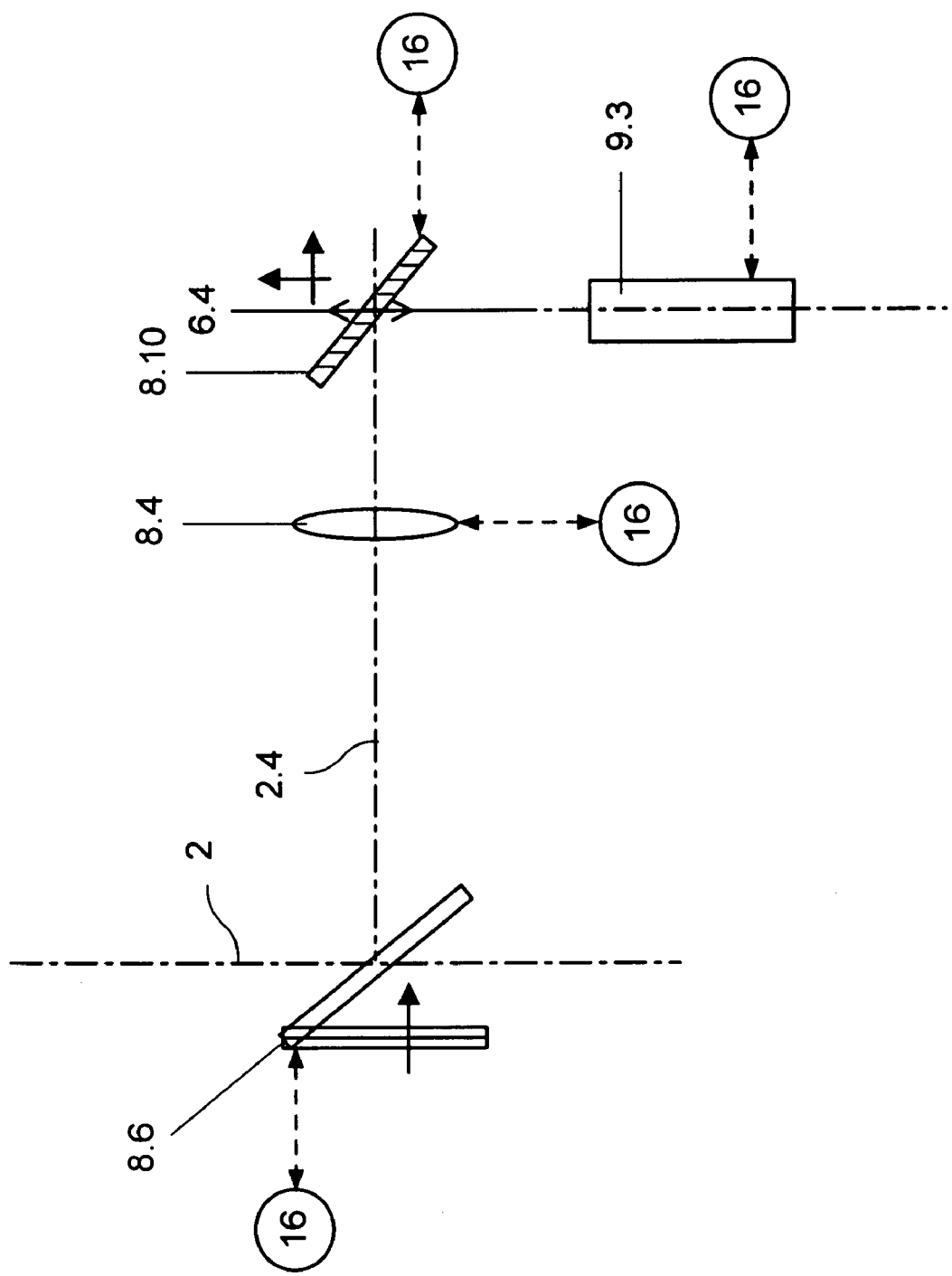
FIG. 9b shows an optical arrangement for a twelfth embodiment example of an apparatus.

A twelfth embodiment example will be described in more detail with reference to FIG. 9b. The drawing shows an arrangement as partial system 2.4 for an irradiation system 2 which can be mirrored into the irradiation system 2 by means of the controllable swing-out mirror 8.6 for therapy as well as for measurements. A therapeutic coagulation laser or measurement laser 9.3, e.g., for laser Doppler measurements, is directed to an xy scanner mirror 8.10 which is arranged in a pupil plane 6.4. The coagulation laser or measurement laser 9.3 can be focused on the irradiated plane 4.1 by means of controllable optics unit 8.4. The interfaces 16 connect the controllable units of the arrangement to the ITS 17.

The combination of necessary diagnostic and examination techniques with therapeutic apparatus in the same device system is a precondition for individualized management and optimization of therapy. Further advantageous inventive effects of the eleventh and twelfth embodiment examples are shown in the following in the description of the cooperation of the apparatus with the methods according to the invention.

Further modifications, the generation of additional partial systems or the exchange of units or of the described EMS 14 with other EMS 14 does not change the essence of the basic inventive idea, but lead to a change in the functional possibilities or variability, expands or limits the breadth of applications.

For example, a xenon lamp in continuous operation is preferably used as irradiation source 9 in order to achieve high luminance. Nevertheless, means for additional flash operation can be advantageous. The irradiation source 9, with its radiating surface and aperture angle in cooperation with its imaging via the optics unit 8.3, can restrict possible variation in the formation of elemental light beams.

The SM 15 were constructed, for example, as filter wheels with known filters. The use of structured filters which are conjugate to an EMS 14 in a pupil plane could also be advantageous. Accordingly, a defined color could be associated with each element of the EMS 14 or each elemental beam bundle by means of the filter structure.

Another advantageous construction of the SM 15 could be controllable polarizers or controllable tunable filters which are arranged in the irradiation system and in the reception system and which make possible, e.g., examinations for autofluorescence or fluorescing dyes whose spectra are not yet known.

Previously, only the use of image-generating receivers was described. It may also be advantageous to use other or additional beam receivers such as photomultipliers or other one-surface or multi-surface semiconductor receivers. High-sensitivity MCP receivers or other systems for single photon detection may likewise be advantageous, as well as CCD line receivers in certain cases.

The multifunctionality of the solution according to the invention is first of all the result of the cooperation between the method according to the invention and the apparatus according to the invention which is realized by the cooperation of the hardware units and software units, already described, of the ITS 17 with the other units of the apparatus.

The method is explained based on an apparatus corresponding to FIG. 7 in which the irradiation system 2 is split into partial systems 2.1, 2.2 and 2.3 corresponding to FIG. 8a.

As was already described, the apparatus shown enable the formation of elemental beam bundles. By elemental beam bundles is meant the smallest beam bundles that can be generated by the apparatus through programming techniques by means of controlling through the ITS 17, e.g., by controlling a respective element of the different EMS 14 which are provided. As was already described, an elemental beam bundle is generated with an EMS in reflection 14.2 by controlling the angular position of an elemental mirror and in that the radiation reflected by the elemental mirror is mirrored into the desired system. With an EMS in emission 14.3 (self-illuminating EMS), the self-radiating elements are switched on directly or are provided with a defined intensity value. When using EMS in transmission 14.1, as in the present embodiment example according to FIG. 7 and FIG. 8a, an element is switched to transmission for every EMS in transmission 14.1. An element with the transmission value 0 can not form an elemental beam bundle. For the EMS as receiver 14.4, only one element needs to be read out by itself. Accordingly, elemental beam bundles can be generated between the elements of the two EMS 14 in the irradiation system or reception system 2 and 1 according to FIG. 7 which are limited only by the surface of the elements of the EMS 14 or images thereof. The direction and position of the elemental beams in the eye 10 are determined only by the position of the controlled elements of the EMS 14 in the planes. The elemental beam bundles can be generated independent from one another between irradiation system 2 and reception system 1 or in the partial systems 2.1 and 2.2 from FIG. 8a. Elemental beam bundles develop within a system or partial system in such a way that each element or its image of the first EMS 14 with each element or its image of the second EMS 14 gives an elemental beam bundle. However, a precondition for this is a suitable irradiation source 9 which is imaged in a known manner in the pupil planes and whose surface fills up the pupil plane and, in addition, illuminates the irradiated plane 4.1.

When only one EMS 14 is used, as in FIG. 5, and a mechanical diaphragm takes the place of the second EMS 14, elemental beam bundles can likewise be generated as was described, but they can only change their position in the plane of the EMS 14, while they are fixed in the plane with the mechanical diaphragm or its images.

Figure 11:
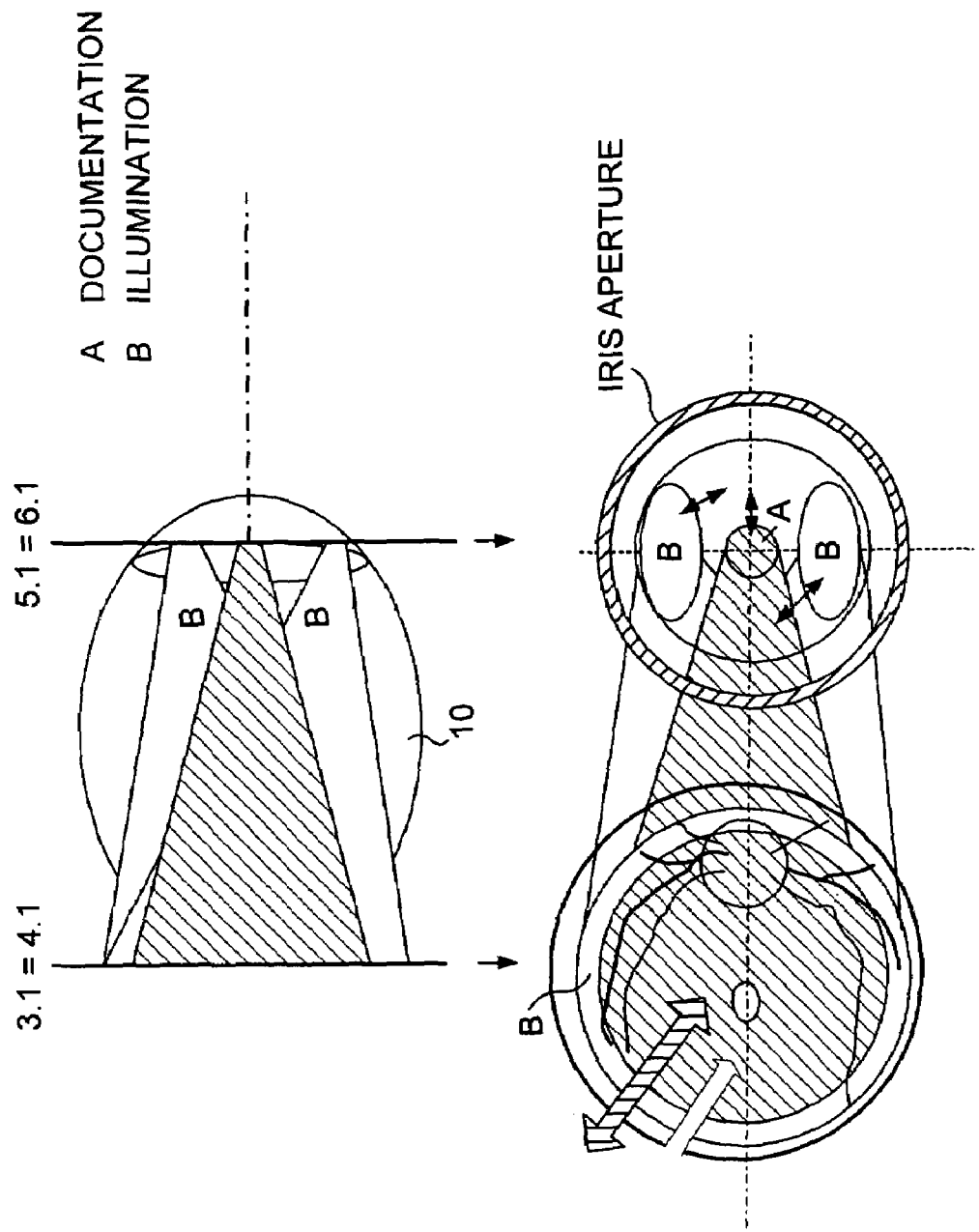
FIG. 11 shows beam bundles in the operation of an apparatus as adaptive retinal camera.
Figure 12:
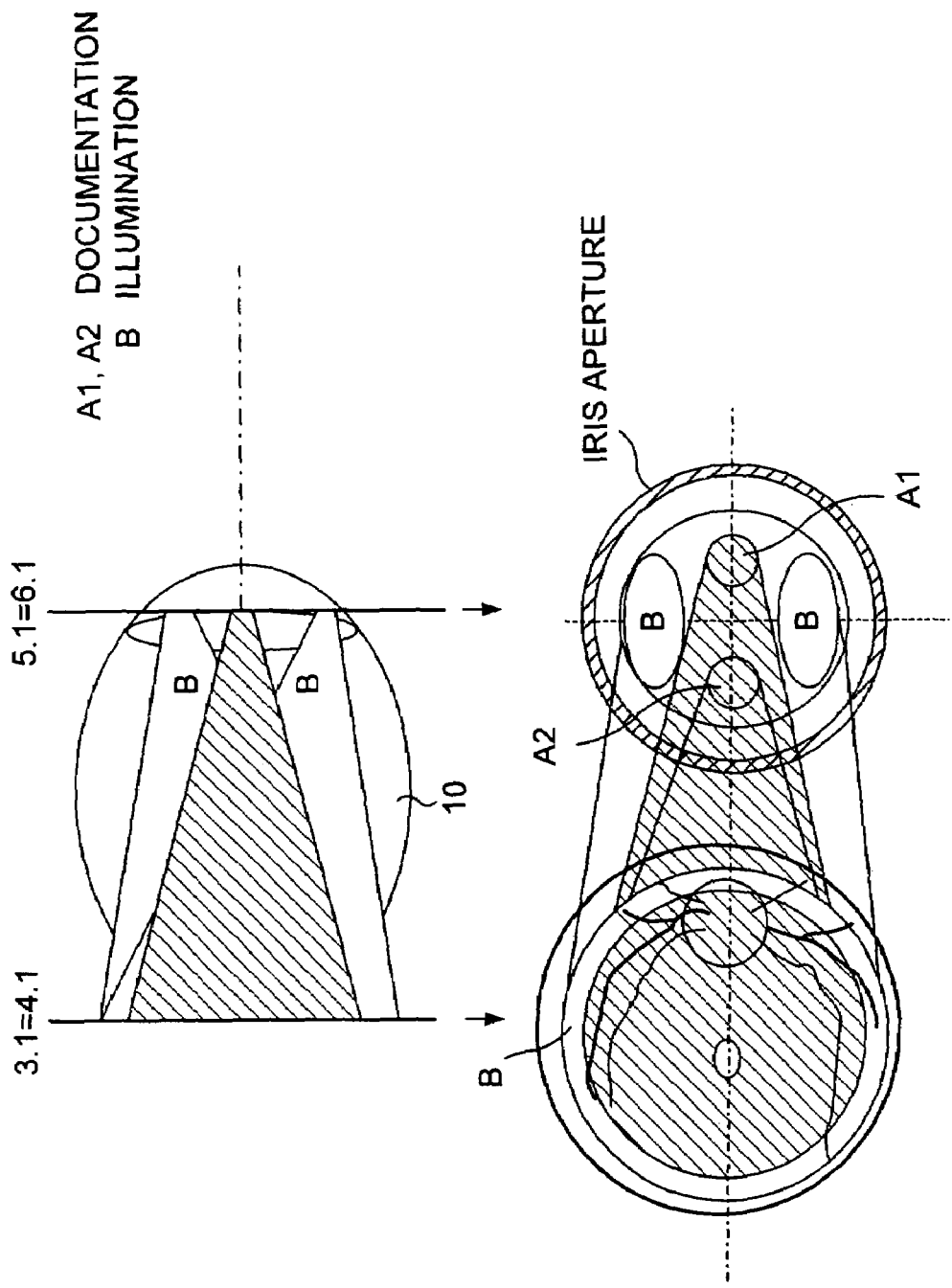
FIG. 12 shows beam bundles in the operation of an apparatus as adaptive retinal camera for stereo documentation of the retina.

By controlling a plurality of adjacent elements of the EMS 14, elemental beam bundles can be combined to form a common beam bundle. By controlling different contiguous groups of elements of the EMS 14, different beam bundles are generated. When one or more beam bundles are generated in such a way that they result in a cohesive functional sense for a device function, this elemental beam configuration is referred to as a functional beam path. A functional beam path can also comprise only one elemental beam bundle. FIGS. 11 to 16*b* show beam bundles belonging to functional beam paths. A functional beam path is needed to realize examination principles. The functional beam paths of a retinal camera are, e.g., the illumination bundles in the irradiation system 2 with which the object plane is illuminated and the imaging bundles by which the object plane 3.1 is imaged in the receiver plane (FIG. 11).

Functional beam paths are, e.g., documentation beam paths, fixation beam paths, measurement beam paths, testing beam paths, stimulation beam paths and therapy beam paths which are obtained by different characteristics of the beam bundles and elemental beam bundles. As was already described, these are characteristics such as the focal planes of the bundles, geometric shape, surface, quantity, intensity and intensity distribution over the bundle, spectral composition and in the pupil plane but also in the object plane 3.1 or irradiated planes 4.1. In addition to this, there is also the time behavior of the bundle and characteristics occurring through the simultaneous or successive cooperation of a plurality of beam bundles inside a system, between the partial systems, and between the irradiation system 2 and the reception system 1. According to the invention, elemental beam bundles are generated by controlling the controllable units depending on the apparatus in different degrees of freedom and by allocating characteristics to functional beam paths. The examination sequence and functional beam path determine the system parameters such as geometric, temporal, photometric and spectral resolution as well as error sources.

Due to the high degrees of freedom of the proposed apparatus, a large number of different functional and still unknown beam paths can be generated as will be shown in the following by additional embodiment examples for the method according to the invention. Different examination processes can be implemented by a device developed by manufacturing techniques only through programming by means of ITS 17. This will be referred to as multifunctionality.

Due to the high time resolution of the EMS 14 which can build more than 1000 images per second corresponding to the current state of technology, very rapid modifications of the functional beam paths for optimizing examinations as well as function sequences can be processed very fast or different examinations can be carried out successively by quickly changing functional beam paths.

In addition, the large number of possible modifications of the beam paths and examination sequences within very short times is a precondition for the functional adaptivity and individual adaptivity and the individual therapy optimization to be described subsequently.

According to the invention, a plurality of functional beam paths and parallel examination processes can be realized simultaneously. In addition, the characteristics are attributed to the elemental beam bundles or beam paths in such a way that the different functional beam paths can be separated from one another again, e.g., geometrically or functionally with respect to color or on the receiver side by correspondingly tuned partial systems or by signal analysis or image analysis. Due to the high time resolution, different beam paths, e.g., also frequencies, can be encoded as was already described. The following embodiment examples for the methods serve as examples for these multiple beam paths.

Further aspects of the method according to the invention will be explained with reference to FIG. 10. FIG. 10 shows a flowchart of an examination process. It is essential that the program run for the examinations by means of the apparatus is not rigid but proceeds by two optimization loops according to the invention, so that it is possible to adapt to distinctive features specific to the patient and specific to the examination. The goal of the examination is predetermined. The respective examination program is selected (program selection) and run through (program run) corresponding to the goal of the examination automatically or based on dialog. The examination program makes it possible to change essential characteristics of the functional beam paths and examination process (optimization of apparatus and method). In addition, pre-examination results or auxiliary examinations are carried out and their results are automatically evaluated and the feedback signals (patient-specific or examination-specific feedback) automatically modify the program run and the functional beam paths (first optimization loop). The effect that can be realized in this way will be referred to as functional adaptivity. The optimizing changes and output data along with the examination results are stored in relation to the patient (patient-oriented storage) and can be used by a knowledge-based, adaptive system (expert system) for automatic optimization of the examination processes. According to the invention, means for artificial intelligence are provided in the program library and data storage.

In a second optimization loop, the operator of the apparatus is given the opportunity to adapt (dialog examiner) the examination process to the individual interview and unique attributes of the patient or of the object being examined in an optimal manner directly or with the assistance of knowledge-based, adaptive systems (programs). These optimizing changes and optimizing parameters are also stored together with the examination results, evaluated by expert systems and made available in patient-specific manner in later examinations. The effect achieved in this way is termed individual adaptivity.

The high flexibility of the apparatus and method can be utilized in a considerably improved manner by connecting the examination processes to an expert system. In so doing, the type of expert system insofar as it is adaptive and/or knowledge-based is of secondary importance for the invention. An expert system is not a mandatory requirement for realizing adaptivity, but assists in a decisive way.

As was already explained, due to the fact that the EMS 14 arranged in the apparatus is controllable with respect to elements, thin elemental beam bundles can be generated on the irradiation side and on the reception side and can be blended in and out as desired and variously manipulated in color, in intensity, in time sequence as well as simultaneously and independently and in particular can be allocated to the different beam paths individually and independently. This was previously possible only to a limited extent, if at all, in conventional examination equipment with correspondingly complicated mechanical-optical design solutions or special mechanical-optical apparatus. In addition, mechanical solutions are very expensive with respect to development and production and are prone to malfunction.

An apparatus according to the invention is basically operated in the following steps (examination process):

Step A: Definition of the goal of the examination and, therefore, of the necessary functional beam paths and their desired system parameters and function for the device principle to be realized with corresponding program call (carried out during the development of the device system by working out the device software for the respective device principle).

Step B: Selection and calling of the program for controlling startup and running, for signal analysis and image analysis, evaluation, dialog operation, functional and individual optimization, for patient-related storage, documentation and results presentation.

Step C: Program-controlled basic adjustment—1st examination period:

Determination of the position of the imaging-side object plane 3.1 and of the irradiated plane 4.1 in the eye 10 for initial starting point by controlling the optics units for focusing and defective vision compensation 7.4 and 8.4. (These optics units serve at the same time as means for displacement of the imaging-side object plane 3.1 and the irradiated plane 4.1 in the depth of the eye 10 and possibly for changing the imaging scale).

Adjustment of the position and geometry of the intersection points of the elemental beam bundles of the individual beam paths for the imaging-side object plane 3.1 in the eye 10 through control and readout of the elements of the corresponding receiver unit(s) in the receiver plane 3.2 conjugate to the object plane 3.1 in the individual reception-side beam paths and/or through adjustment of magnification by means of optics unit 8.1.

Adjustment of the position and geometry of the intersection points of the elemental beam bundles of the individual beam paths for the irradiated plane 4.1 by controlling the elements of the corresponding EMS 14 in a plane conjugate to the irradiated plane 4.1.

Adjustment of position and geometry of the intersection points of the elemental beam bundles of the individual beam paths through the plane of the eye pupil by controlling the elements of the corresponding EMS 14 in a plane conjugate to the eye pupil.

Allocation of the elemental beam bundles to functional beam paths and assignment of the characteristics described above, e.g., intensity, color, degree of polarization, frequency, etc., to characteristics corresponding to the provided controllable means of the arrangement.

Processing the program for signal analysis and image analysis, evaluation, dialog operation, functional and individual optimization, for patient-related storage, documentation and presentation of results for the current processing period.

Step D: Control of the examination process through repetition of the periods (Step C) by varying the adjustment 1-5 and implementing point 6 until the examination process is concluded.

The manner is which control is carried out is known from the prior art. The adjustments according to the invention and the respective basic principle of the processes according to the invention which are sufficient for realizing various constructions of the invention by prior art means are described in the following.

The apparatus according to the invention can advantageously be operated as an adaptive retinal camera. The functional beam paths are shown schematically in FIG. 11. The preceding embodiment examples for the apparatus, particularly according to FIG. 6, serve as basis.

The main function of a retinal camera is image documentation for different magnifications, image fields and areas of use. Areas of use are in standard image documentation in white or colored light, fluorescence angiography or ICG angiography and the recording of autofluorescence.

The operation of an apparatus as retinal camera is basically the same as in Steps A to D which can be described concretely in the following manner.

The planes 3.1 and 4.1 are situated in the same plane by means of the adjustment of units 7.1 and 8.1 or 7.4 and 8.4.

The overview adjustment of 50° is preadjusted (surface B) as basic adjustment of the irradiated plane 4.1 and the object plane 3.1, while the reception-side surface A is selected so as to be slightly smaller. Both surfaces are adjusted via the respective EMS 14 as circles.

In this case, the illumination-side aperture surfaces are constructed as two separate oval surfaces B and the reception-side aperture is constructed as a central circle A.

Depending on the construction of the device, the irradiation-side unit can temporarily switch all elements to bright for documentation of the retinal image (surface A) or, instead of the irradiation source 9, a flash lamp is swung into the beam path for recording.

In the dialog mode, the operator can select the surface to be documented in stages or continuously (when zoom optics are provided in 8.4 and 7.4) the magnification and the image field section. Any color can be adjusted with the SM 15 in dialog operation.

In the following functional adaptation, the sequence control is also necessarily changed so as to be adapted to the changed or additional functions.

The conventional retinal camera principle with fixed diaphragms, fixed image fields and fixed filters (predetermined filters for color recording, fluorescence angiography and ICG angiography which can be inserted or swung in) is realized by its fixed adjustments with only a few adjustments for an apparatus according to the invention.

In contrast, the apparatus according to the invention operated as a retinal camera can be adapted to the clinical interview in a desired manner (functional adaptivity).

The free programmability of the irradiated plane 4.1 makes it possible to adapt the adaptive retinal camera to any receiver geometries. In the retinal camera of the prior art, round image fields are customarily used so that valuable pixel surface of the rectangular receiver surfaces is lost.

Another example for functional adaptivity is the solution of the problem of limited dynamic range of conventional retinal cameras with electronic imaging, the dark areas of the retina (macula area) and the light areas (optic disk) can not be adequately resolved simultaneously or documented without overradiation in an image. For example, in order to simultaneously resolve the bright pupil and the dark foveola photometrically in an optimal manner, different recordings must be made with different exposures due to the limited dynamic range with known retinal cameras.

The individual surface regions of the retina can be illuminated with different degrees of brightness with the adaptive retinal camera. The necessary adjustment by means of the illumination-side EMS in transmission 14.1 can be controlled manually by the examiner while visually monitored on the monitor; but preferably a brightness correction image is determined automatically by means of the evaluation of the actual images during the adjustment and is adjusted by the elements of the EMS in transmission 14.1, the illumination in the fundus image is corrected virtually continuously and is adapted to the dynamic range of the receiver. Differences in illumination can also be corrected in this way. This results in an image that is corrected on the illumination side and in which all surface elements are recorded with optimal control of the receiver. According to the invention, the brightness-modulated image with the illumination-corrected image can be calculated afterwards and an image can be generated with a higher dynamic range than that permitted by the receiver.

The adaptive retinal camera also makes it possible to vary the depth of field in any way and with high sensitivity by changing the reception-side (and irradiation-side) aperture opening so as to be adapted to the clinical interview. Optimal wavelengths for determined diseases can be preadjusted automatically by means of continuously adjustable SM 15 when the presumed diagnosis is entered along with the goal, for which optimal wavelengths are found in a stored list (knowledge-based system).

Another possibility consists in making the illuminating and receiving surface (see arrow in FIG. 11) very small. In this way, small surfaces at the fundus can be documented and examined with high contrast and high magnification and the necessary brightness can be carried out by controlling the elements of the EMS in transmission 14.1 and/or additionally by controlling the aperture openings of reception-side and irradiation-side beam path. In this way, according to the invention, an image field scanner can be realized. The small image fields can be read out either successively or simultaneously at the receiver. Successively generated images can be put together with the coordinates of a sequence system (see below) automatically to form extremely high-resolution panoramic images. High-resolution images of this kind could be produced by conventional cameras only by means of image montage for reasons of light loading. When the surfaces are reduced to one element, a confocal scanner with conventional light source is obtained. For this purpose, the process must be controlled such that the readout of the receiver elements is controlled with respect to its time sequence in such a way that the irradiated surfaces in the irradiated plane 4.1 always coincide exactly with the scanned surface in the object plane 3.1 or, depending on the scanner image that is produced, have a defined position relative to the illuminated surface. However, by changing the examination process (functional adaptivity), the position of the focal plane of the irradiation and reception system 2 and 1 can also be changed in depth at the same time and topological information can accordingly be obtained and various layers can be examined depthwise. On the other hand, only one light section can be generated on the irradiation side and is scanned on the reception side along the beam bundle in the eye 10. When the position of the receiver elements scanned in the object plane 3.1 is not situated on the illuminated surfaces in the irradiated plane 4.1, examinations can be carried out in regredient or retrograde light. These examinations can be carried out simultaneous with the light scanner.

As a further example for functional adaptivity of the apparatus, this apparatus is operated as adaptive retinal camera for stereo documentation of the retina. An apparatus according to FIG. 6, whose reception system 1 is divided into partial systems 1.1 and 1.2 corresponding to FIG. 8c, can be used advantageously for this purpose. The functional beam paths are shown schematically in FIG. 12.

Previously in conventional retinal cameras in stereo recordings the aperture openings (FIG. 11, A), usually in the center, were only divided by means of deflecting unit. The disadvantage is a very small stereo basis. The aperture openings A1 and A2 (see FIG. 12) are generated, respectively, for one of the stereo beam paths with the adaptive retinal camera for stereo documentation of the retina by controlling the reception-side EMS 14. The surface size and the distance between pupils A1 and A2 can be modified in any desired manner for functional optimization.

Figure 13:
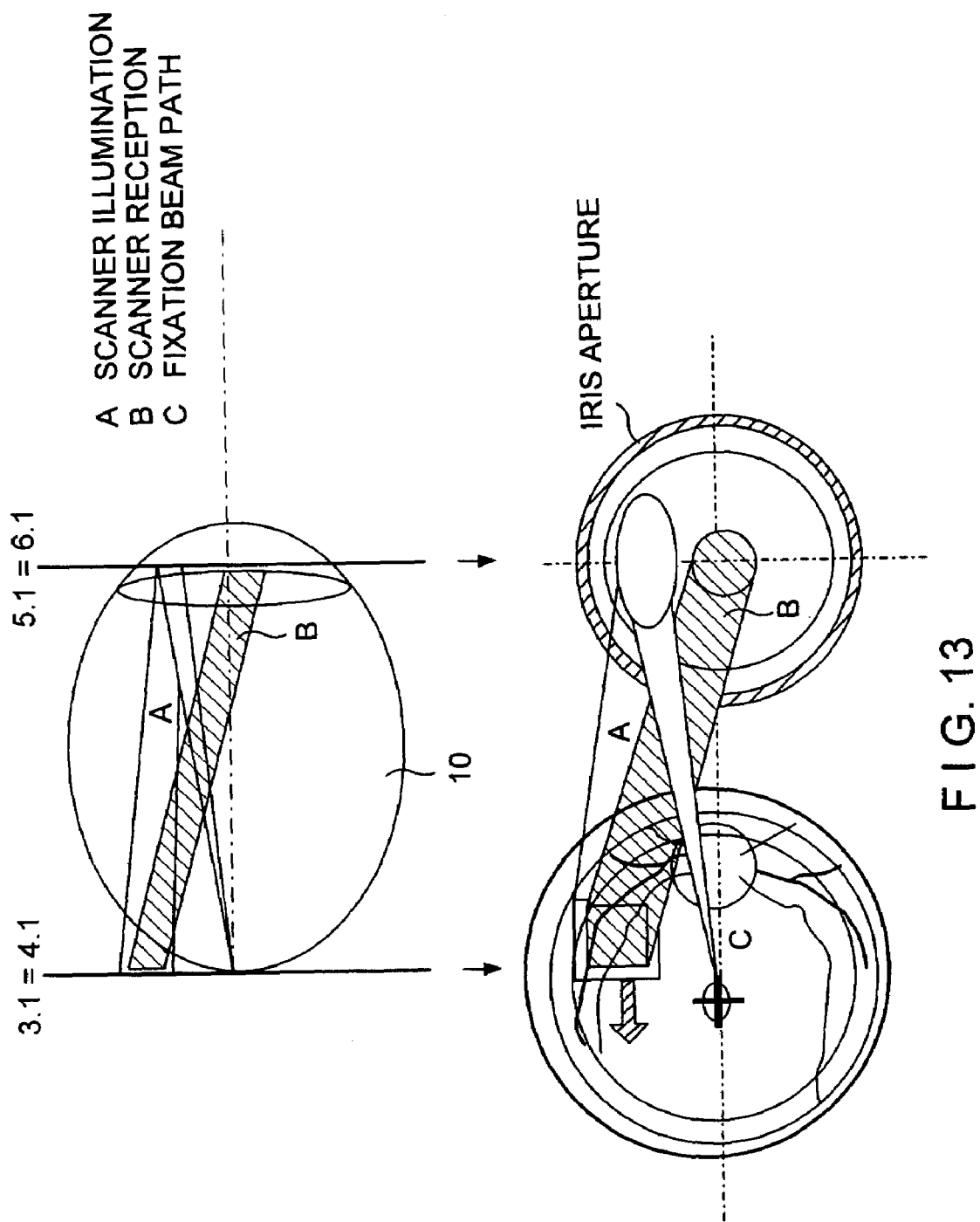
FIG. 13 shows beam bundles in the operation of an apparatus as image field scanner with fixation beam path.
Figure 14:
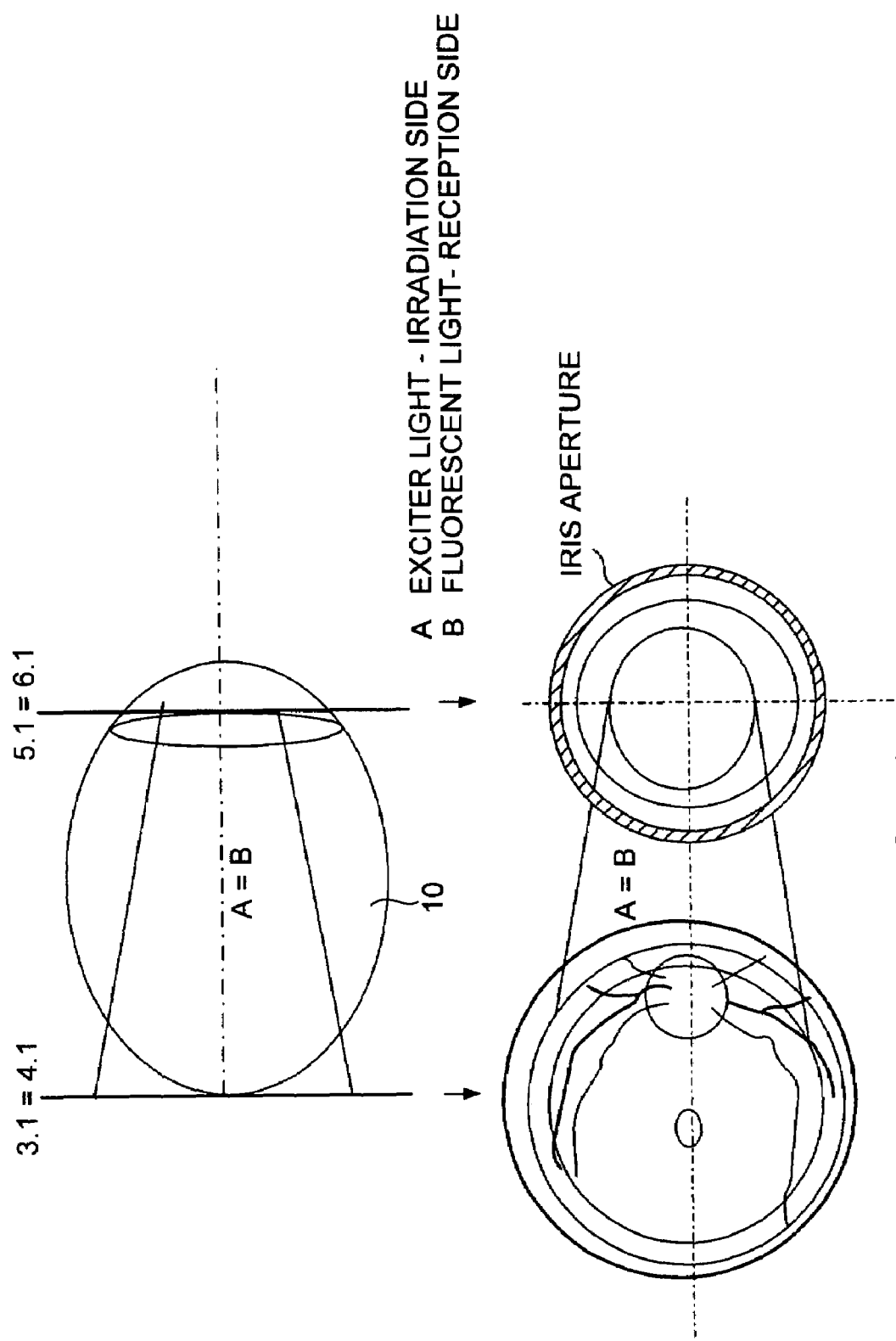
FIG. 14 shows beam bundles in the operation of an apparatus for fluorescence examinations.

As an example for functional adaptivity and the realization of multiple beam paths through programming technique, the generation of an additional beam path, a fixation beam path, will be described. The elements of any geometry which are defined as fixation marks are given, e.g., by characteristics which are particularly perceptible by the eye of the patient. Such a characteristic can be, for example, the blinking of the defined elements inside the visible irradiated surface 4.1. The mark can be displayed on a dark background simply by means of differences in intensity, or a color which can stand out from its surrounding field can be assigned to it. The desired fixation coordinates or the desired fixation mark movement is entered in dialog mode or in stored comparison examinations. Beam bundles for an apparatus operated as an image field scanner with fixation beam path are shown in FIG. 13.

Another problem in conventional retinal cameras is the focusing of the retinal recordings, particularly with angiographic recordings. The realization, according to the invention, of multiple beam paths and of the possible rapid change in functionality allows continuous monitoring of the state of focus in that the position of the focal plane is determined and, if need be, automatically readjusted by optics units 7.1 and 8.1 through programming simultaneously or successively between the recordings, e.g., according to the principle of Scheiner diaphragms. The functional beam path of the Scheiner diaphragms simultaneously realizes a refractometer which can also be constructed as an independent examination function. For this purpose, again, the beam bundles need only be generated through programming technique with the two necessary radiation-side aperture diaphragms, while the receiver supplies the signals or images which are evaluated by signal analysis or image analysis with respect to the coincidence (change in the deflective vision compensation) or the spacing of the Scheiner beam bundles at the fundus. Also, a refractometer of this kind would be very functionally adaptive in that the Scheiner diaphragm apertures and their position in the eye pupil, their relative spacing and their number can be adjusted through programming technique. Finally, functional beam paths for examining imaging errors of the eye can also be realized (abberometer).

The functional adaptivity of the apparatus also allows fluorescence examinations to be carried out. In this case, with the SME 15 as controllable tunable filter (FIG. 7), any desired combination of exciter filters and blocking filters can be adjusted on the one hand within the framework of a tunable wavelength, while the aperture diaphragms can be arranged so as to be covered by the irradiation beam path and reception beam path (see FIG. 14) and can be made very large. The pupil size can then be adjusted again as a compromise from photometric resolution, geometric resolution, time resolution and spectral resolution. Accordingly, the advantage over conventional retinal cameras consists not only in the fixed exciter/blocking filter combinations, but also in the free selection of optimizing criteria and the more favorable situation with respect to light yield.

Particularly for the examination of autofluorescence, the invention with freely selectable exciter filter and blocking filter combinations offers important advantages over the limited possibilities of conventional cameras.

Apart from the high functional adaptivity, the apparatus according to the invention has a high individual adaptivity in connection with the method according to the invention.

The achievable image quality is not only dependent on the interview and consequent modification of the examination technique, but is decisively determined precisely in the case of ill patients by the individual factors specific to the eye of the patient. For example, it is known that the dependence of the resolution of the eye 10 upon the aperture of the actively imaging beam bundle, upon the position of the aperture on the cornea, and upon the beam passage through the eye 10 varies sharply on an individual basis. Further, turbidity can render documentation of retinal images with conventional retinal cameras completely impossible.

Due to the fact that the pupil apertures can be optionally controlled and rapidly switched with respect to their diameter and also with respect to their position in the eye pupil, the adjustment of pupil sizes, pupil position and image field sizes, optimal contrast and resolution can be achieved with the invention and portions of the fundus can also be documented in difficult cases with usable results. According to the invention, an individual optimization of light load, contrast, resolution, image field, photometric and time resolution can be achieved by matching the aperture diameters of the reception-side and irradiation-side pupils. As was already described, the wavefronts can also be modified (wavefront correction) and therefore the achievable resolution can also be increased. The solutions according to the invention also make possible the realization of principles for measuring the wavefront deformation.

The apparatus according to the invention can advantageously be operated as a light scanner. The functional beam paths are shown schematically in FIG. 15. The known conventional scanners scan the fundus of the eye with laser light. The advantage consists in high-contrast recordings from different planes. A substantial disadvantage consists in the loss of color information, Also, three additional laser wavelengths would only generate an apparent color image, since the scanning is still carried out only with a very narrow-band spectrum. Essential information in spectral changes of different wavelength ranges is also lost with three narrow-band scanning beams.

The operation of an apparatus as light scanner is carried out fundamentally by Steps A to D and can be described concretely as follows:

Planes 3.1 and 4.1 are situated in the same plane by means of the optics units 7.4 and 8.4.

The basic adjustment of the irradiated (illuminated) field at the fundus of the eye is reduced to minimum size (element size) for the irradiation-side bundle. The reception-side surface is preferably adjusted equal to the radiation-side surface with respect to planes 3.1 and 4.1.

Depending on the type of operation, the irradiation-side aperture surface or the reception-side aperture surface is situated in the center or off-center.

The pupil surface is preadjusted relying on the retinal camera. Depending on the type of operation, two illumination-side beam bundles can also be used which must meet in planes 3.1 or 4.1 according to definition (FIG. 15).

By controlling the EMS in transmission 14.1, or the receiver, conjugate to the planes 3.1 and 4.1, the scanning surfaces at the intersection of all bundles are moved over the plane. The plane to be scanned is adjusted with respect to depth by means of the optics units 8.4 and 7.4 in order to obtain images from different layers. Due to the elements of the receiver, confocal ratios are created conjugate to the elements of an irradiation-side EMS in transmission 14.1.

Also, in this case, the actively imaging beam paths can be optimized corresponding to the interview through a compromise between geometric, photometric and time resolution, light load and image field in that the position, size and shape of the surfaces of the beam paths in the eye pupil are optimally adjusted like the illuminated and received surface elements in the eye. The beam path that is not actively imaging can make use of virtually the entire eye pupil area apart from a small safety distance. With the SM 15 as controllable tunable filter, it is possible to operate in fluorescence mode or normal scanning mode and to adjust different wavelengths for scanning.

Again, this adaptive light scanner can also be connected to additional beam paths for measuring, documentation and stimulation.

Depending on desired imaging characteristics, the receiver, for example, can be changed. For example, an EMS in transmission 14.1 can preferably be used instead of the EMS as receiver 14.4 in the receiver plane and a photomultiplier which registers the switched through light in its entirety as signals with high sensitivity can be arranged behind the EMS in transmission 14.1. In this case, it would also be possible to work with mirror arrays (EMS in reflection 14.2). The signal is subsequently composed again for the image section analogous to the known SLO. In addition to the irradiated retinal surfaces, the remitted light of adjacent retina can also be combined to form an image with a receiver array as well as with a photoreceiver by suitable control depending on the desired mode of operation.

By means of the functional adaptivity of the overall system, images with adjustments can preferably be prepared as retinal cameras and smaller retina areas can be examined in a scanning manner according to a preset.

In order to eliminate distorting influences, additional infrared recordings are preferably generated simultaneously and the displacement coordinates conditioned by eye movement between two scanning positions are formed from these additional infrared recordings. These displacement coordinates are used as feedback for correction of eye movements by means of the correction of scanning movements or for correction in the composition of the image.

Figure 16A:
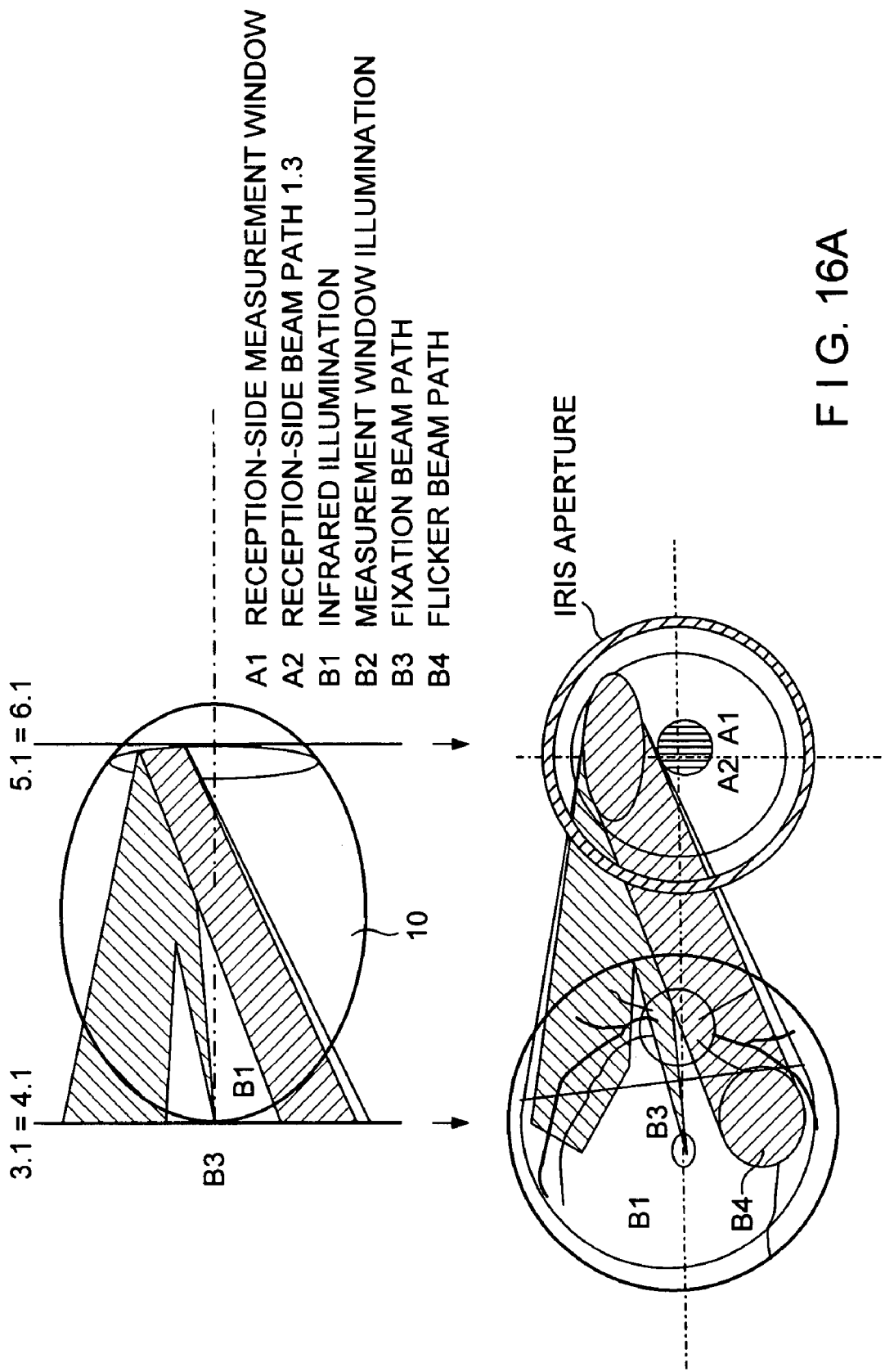
FIG. 16a shows beam bundles in the operation of an apparatus for functional imaging of the retina.
Figure 16B:
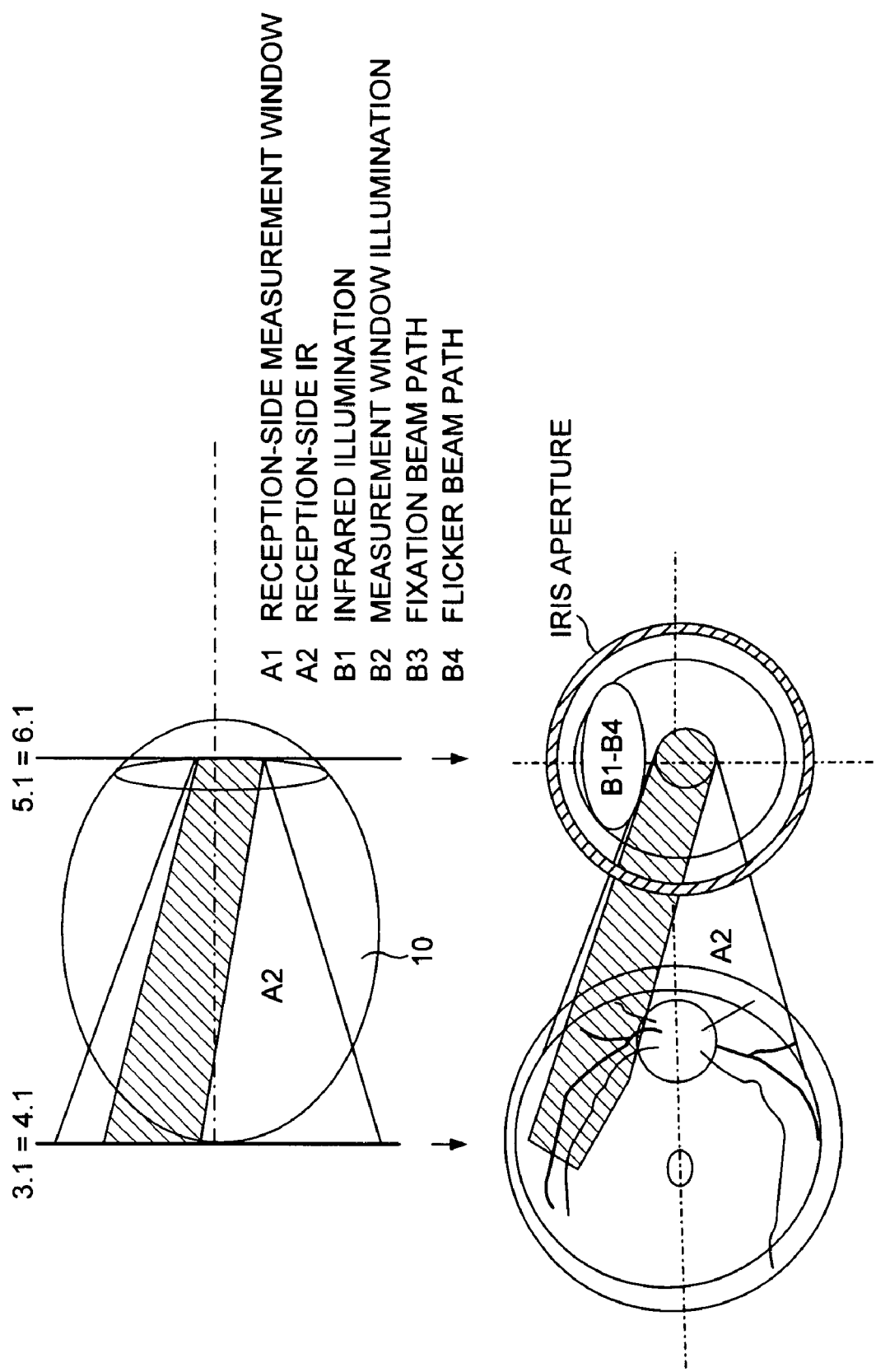
FIG. 16b shows other beam bundles in the operation of an apparatus for functional imaging of the retina.

Beam bundles such as those advantageously generated for the operation of an apparatus as a device system for the functional imaging of the retina will be described with reference to FIGS. 16a and 16b.

By retinal functional imaging is meant the display of measurement results for functional characteristic quantities associated with the structures of the retina, wherein the measurement results or the measurement values or test values can describe the functions of metabolism or vision or microcirculation (micro-blood flow) in a definite manner. Various measurement systems for detecting metabolism, micro-circulation or visual function which are built up by subsequent modification of known retinal camera technique are known from the prior art. The measurement characteristics are rigidly defined in terms of manufacturing technique and design by the basic construction of conventional retinal cameras, so that it is not possible to adapt to the individual peculiarities of the patient's eyes in particular.

The following configuration of the method in connection with an apparatus will represent adaptive systems for functional imaging and for measurement and testing systems for the eye 10.

Preferably, a documentation beam path, a fixation beam path, a stimulation beam path, a measuring and testing beam path, and a beam path following the eye are needed as functional beam paths for function imaging, although a measuring system with only the measuring and observation beam path for adjusting the measurement point and for measuring would already be sufficient for operation within the strict meaning of the invention.

The object plane 3.1 and the irradiated plane 4.1 are situated in the same plane. Similar to the adaptive retinal camera, the irradiated plane 4.1 is preferably adjusted with the EMS in transmission 14.1 and the SM 15 as controllable tunable filter in the partial system 2.2 (see FIGS. 7 and 9a). The irradiated surface in the eye 10 is initially situated on the maximum possible surface for overview and appears as a circle, while the reception-side surface in the object plane 3.1 is situated in the irradiation-side surface of the partial system 2.2. The maximum receiver surface of the EMS as receiver 14.4 is adjusted only slightly smaller that the irradiation-side surface. At the same time, an infrared illumination is generated with the partial system of the irradiation system 2.3 in the irradiated plane 4.1 which illuminates the maximum image field area as a circle. For this purpose, a physical diaphragm should be arranged in the plane 4.2 of the beam path 2.3 conjugate to 4.1. The infrared part is superimposed on the irradiated field on the eye 10 as was already described.

Further, a fixation beam path is generated by adjusting the EMS in transmission 14.1 in the partial system 2.1. A visible mark is programmed. The characteristics of the fixation beam path are adapted to the examination, e.g., blue flicker light is selected (control of the SME 15 in 2.1).

In this case, the illumination-side aperture surfaces are initially formed as oval surfaces (B). In the present case, all irradiation-side beam components pass through this aperture opening in the eye 10.

The reception-side aperture is constructed as a central circle.

The receiver 14.4 of the partial system 1.1 which is controllable independently with respect to element (pixel) is switched to reception of the entire image of the object plane 3.1. The infrared beam path is spectrally blocked. In addition, the SM 15 of this partial system is adjusted during the measurement in such a way that only the measuring light (no flicker light and no fixation light) reaches the receiver. The infrared receiver is likewise switched to reception.

The examiner can selectively use the infrared image or the image in the visual spectrum for subsequent adjustment. The position of the fixation mark is controllable by the examiner. With the image, the examiner can carry out the adjustment of the area of the fundus to be examined. Parallel to this, the infrared image is evaluated by its ITS 17 with an eye follower on the software side which supplies the displacement coordinates given by the eye movement between the images in real time.

The examiner marks the measuring window in dialog mode, e.g., with the mouse, and the measuring window is indicated on the monitor superposed with the retinal image. The EMS in transmission 14.1 in the partial system 2.2 obtains the coordinates of the measurement window and darkens all other areas outside of the measuring window for reducing the light load. At the same time, the necessary spectral matching of the measuring light is carried out by means of controlling the SM 15. The online measuring process, e.g., the analysis of the vessel portions in the measuring window area, is started and realized by means of measuring and evaluating programs. For this purpose, the EMS as receiver 14.4 is controlled in such a way that it no longer reads out and transfers the elements of the entire image, but only those of the measuring surface. At the same time, the displacing coordinates given by the eye movement of the eye follower program which likewise operates in real time are used to correct the position of the measuring surfaces. The examiner sees how the measuring window in the image runs along with the eye movements. Functional characteristic values for functional imaging are obtained in particular when a function of the retina is disturbed or exercised. This can be achieved, for example, by different stimuli with light, which is sufficiently known from electrophysiology on the eye 10. Stimulus possibilities of this kind can be realized only to a very limited extent, if at all, with conventional cameras. According to the invention, any timed, color, geometric patterns or objects can be generated for function testing or interference in a static or moving manner simply by programming. In order to set stimuli during measurement, in this case, for example, the unit 14.1 of the partial system 2.1 is controlled in addition to the fixation beam path for generating the stimulation beam path. For functional diagnostics of the vascular system, for example, a blue light should be flickered on a round surface under the macula at 13 Hz for 10 s. For this purpose, the elements of the flicker surface are turned on and off, whereas the fixation beam path remains independent from the flicker light. The beam paths present at the moment that the flicker surface is made bright are shown in FIGS. 16a and 16b. Like the measuring surface, the flicker surface tracks the eye movements by means of the eye follower.

After the flicker response of the desired vascular portions is recorded by the measuring process, the apparatus according to the invention is controlled like a retinal camera for documenting the retinal image, measuring window position and flicker surface position; however, the measuring window and flicker window are emphasized in the image with respect to color and intensity. The measuring and flicker window continue to be tracked in the background until the documentation is concluded. The measurement results are evaluated with respect to the functional characteristic data and the functional characteristic data are graphically presented in the image of the fundus of the eye. In this way, the physician can have a quick overview of the functional limitations.

The advantages of the high degree of functional and individual adaptivity of the system according to the invention become noticeable particularly for complicated measuring processes and testing processes. With the previous method based on known retinal cameras, the described measurements would not be possible. The realization of the many parallel beam paths alone would result in considerable expenditure. The functional adaptivity of the system according to the invention makes possible an important reduction in the light load particularly with longer measuring times or testing times by limiting the illumination to the measuring window. Limiting the receiver pixels to be processed to the measuring window drastically reduces the times for image analysis and signal analysis and first makes possible real-time examinations, e.g., for vascular analysis in state of the art PC technology. The simultaneous eye follower reduces measuring errors through position correction of the measuring window and increases the measurement resolution over the location. The action of the eye follower can be considered as individual adaptivity, since the error influences of the eye caused by eye movement which bring about considerable scattering individually can now be substantially reduced by measurement. At the same time, the pupil positions and sizes can now be optimized corresponding to the individual requirements for the brightness of the image, for resolving capacity, depth of focus and also as a function of the individual characteristics of the eye 10. The adaptivity can be further increased when the measuring windows follow their own goal with their own strategies based on the aim of the physician and follow the changes which may not always be detectable in the image. With respect to examination of the vascular system, one or more measurement fields can automatically follow the vessels and analyze the entire vascular system.

Additional beam paths can be generated simultaneously or only temporarily such as, e.g., additional measuring windows with other measuring principles, refraction measurements, monitoring and correction of displacements of the vascular system toward the eye, adaptation of the pupil positions to a drooping eyelid, to different accommodation states or individually large or small pupil diameters (free diameter of the iris of the eye) and the realization of optimal system parameters.

The apparatus can also be operated advantageously as a nonmydriatic camera. The main function of a nonmydriatic camera is retinal documentation with compact pupils. The adaptivity of the solutions according to the invention also enables this function through programmed adjustment of the apparatus. The construction of the apparatus according to FIG. 7, in which the irradiation system 2 corresponding to FIG. 8*a* and the reception system 1 corresponding to FIG. 8*b* are divided into partial systems, is favorable in this case.

The method according to the invention for programming a nonmydriatic camera proceeds by the steps defined in the beginning.

Fixing of the Position of Planes 3.1 and 4.1 in the Depth of the Eye 10:

The image fields 3.1 and 4.1 are situated in the same plane by means of adjusting the optics units 7.1 and 8.1 or 7.4 and 8.4.

Adjustment of the Position and Shape of the Irradiated and Received Surfaces of Planes 3.1 and 4.1:

The basic adjustment of the irradiated (illuminated) field of the fundus is set to the desired field size. The reception-side surface (object field A) is adjusted slightly smaller than the irradiated field. The irradiation-side surfaces provided over the two units EMS in transmission 14.1 for infrared adjustment and documentation are preferably identically constructed. The nonmydriatic camera is controlled and its images are delivered to a monitor for observing the retinal section.

Adjustment of the Position and Shape of the Aperture Surfaces in the Eye Pupil (Planes 3.1 and 4.1):

The aperture surfaces on the side of the irradiation light are formed, for example, as two oval surfaces (B) similar to the adaptive retinal camera. The reception-side aperture as central circle (FIG. 11). The first functional beam path is the generated infrared illumination and the infrared imaging through the partial systems 2.3 and 1.3 which display the infrared images on a monitor for the examiner and are used for adjustment.

Control Structure

For purposes of adjustment, infrared light is adjusted as illumination in the second illumination-side beam path. Additional functional beam paths serving for flash illumination and imaging in the visual spectrum are generated by means of the partial system 2.1 and 1.1. The color desired for documentation can be adjusted by means of SM 15. The color desired for documentation is adjusted by means of controllable tunable filters.

A fixation beam path is preferably generated through programming technique, as was already described, by means of the irradiation-side beam path.

In addition, the position of the focal plane is preferably determined, as was already described, by means of the infrared second irradiation-side beam path alternately with the infrared image and is corrected automatically for the receiver and the irradiation-side planes by means of units 8.4 and 7.4.

After adjustment has been completed, recording is carried out with the EMS as receiver 14.4 or with a CCD receiver 13.1. For this purpose, the elements of the EMS in transmission 14.1 of the infrared beam path in the second irradiation-side partial system 2.2 is blocked for the beam path and the elements of the EMS in transmission 14.1 of the documentation beam path in the first irradiation-side partial system 2.1 are switched on in the manner of a flash or opened for an additional flash beam path. The image is read out, displayed and stored. The second partial system is available for further functional beam paths, e.g., for refraction determination or for the realization of a fixation beam path.

Functional and Individual Adaptivity

Functional adaptivity is exhibited in the additional beam paths that can be realized for fixation and for automatic focusing. Individually, the image quality can be optimized analogous to the adaptive camera.

Another advantageous operation of the apparatus can be carried out by coupling in an adaptive therapy beam path.

The combination of therapy beam path with imaging or measuring or testing or stimulating methods is very important because it creates essential preconditions for an individually controlled and optimized therapy. The state of the art is defined by separate therapy devices for the fundus which are usually coupled with slit lamps and in which the beam guidance is currently carried out exclusively manually by the physician. The separation between the image of the fundus and the therapy device results in additional substantial disadvantages.

The solution according to the invention for adaptive therapy beam paths overcomes the disadvantages of the prior art. It is advantageous in this instance to use the embodiment example for an apparatus according to FIG. 7 in which the irradiation system 2 corresponding to FIG. 9*a* and FIG. 9*b* and the reception system 1 corresponding to FIG. 8*b* are divided into partial systems. A micromirror array as EMS in reflection 14.2 is preferably used as a beam splitter 12 in a plane conjugate to the eye pupil, its elemental mirrors being continuously adjustable individually and independently from one another with respect to their angular adjustment in the x and y direction. The xy adjustment can also be achieved by means of two micromirror arrays which deflect in only one direction and which are imaged within one another with the deflection directions perpendicular to one another. The parallel laser beam can accordingly be focused by means of controlling the elements of the second EMS in transmission 14.2 and the swing-out mirror 8.6 in all points of an image field plane area in the irradiated plane 4.1 in the eye 10. The beam path is mirrored into the irradiation beam path by means of a preferably semitransparent swing-out mirror 8.6. The method proceeds in the following manner:

Fixing of the Position of Planes 3.1 and 4.1 in the Depth of the Eye 10:

The object plane 3.1 and the irradiated plane 4.1 are situated in the same plane by means of adjusting the units 7.1 and 8.1 or 7.4 and 8.4.

Adjustment of the Position and the Shape of the Irradiated and Received Surfaces of Planes 3.1 and 4.1:

The basic adjustment for the functional beam paths of the irradiated (illuminated) field at the fundus are adjusted in the partial systems 2.1 and 1.1 similar to a retinal camera through the EMS 14. In addition, the infrared beam paths are activated as additional functional beam paths for correcting eye movements. The fundus is situated on an image field of 50° (surface B) for an overview adjustment, while the reception-side surface (A) is selected so as to be slightly smaller. Both surfaces are a circle. According to FIGS. 9a and 9b, the additional apparatuses, already described, for generating therapy beam paths are provided as temporary additional functional beam paths. The image of the irradiation-side second beam path, insofar as it is used, and the laser focus of the third partial system 2.3 overlaps the image of the irradiated plane 4.1.

Adjustment of the Position and Shape of the Aperture Surfaces in the Eye Pupil (Planes 3.1 and 4.1):

The irradiation-side illumination-side aperture surfaces are formed in this case as two oval surfaces B. The reception-side aperture is formed as a central circle. (FIG. 11).

Aperture openings of the therapy beam bundles of the parallel partial systems 2.2 and/or 2.3 are superimposed on these aperture openings.

Control Structure

The apparatus is preferably initially controlled like an adaptive camera or like a system for functional imaging. After examinations and documentation of findings, the retinal areas to be treated are marked in the image or criteria are indicated for local examination results which fix determined local areas as therapeutic irradiation areas as defined by the physician. In the latter case, the automatic search can be carried out by means of ITS 17 using different examination techniques according to these areas. When these retinal areas are detected, the coagulation area of irradiation area is marked for the examiner who then initiates and, as the case may be, can stop therapy. According to the invention, two forms of therapy can be realized by means of the proposed solutions: coagulation, e.g., in retinal detachments and diabetic retinopathy (also subliminal coagulation), and irradiation as in photodynamic therapy (PDT). The partial system 2.3 is preferably provided for coagulation, while the partial system 2.2 is provided additionally for coupling in a laser beam path, preferably for PDT.

The therapy can be carried out in an automatically or manually controlled manner in that the swing-out mirrors 8.6 mirror in the respective beam paths and the continuous AMD laser is switched on (PDT) or the laser flash is initiated for coagulation.

Functional and Individual Adaptivity

Functional adaptivity is realized again by means of the high degrees of freedom for the adjustment of system parameters and variation of therapy beam paths and through implementation by means of programming technique in contrast to the prior art, because various additional examination processes or function beam paths such as spectral measurements, circulatory measurements, methods of functional imaging, generation of a fixation beam path, fluorescence angiography, etc. which can run so as to be controlled solely by programming technique at an apparatus according to the invention as adjustment aids for diagnosis and particularly for locally defined therapy indication with a very short time and whose results are used, according to the invention, directly as feedback signals for controlling the course of treatment for changing or adjusting the system parameters of the therapy beam paths corresponding to the distinctive features of the individual patient.

Further, additional beam paths can be generated simultaneously or consecutively, e.g., automatic focusing and fixation beam path. But monitoring and correction of eye movements can also be carried out as described later on. The functional adaptivity with respect to therapy presents another new qualitative feature. The inventive effect will be explained through the example of PDT and coagulation.

PDT

Based on the evaluation of fluorescence angiograms, the surfaces to receive therapy can be defined manually as circular surfaces. The therapy is carried out on another conventional device based on image documentation for diagnosis and therapy indication corresponding to the prior art.

By means of the solution according to the invention, the surface to receive therapy can be exactly defined immediately after examination manually by the physician or automatically by means of corresponding evaluating programs. The coagulating surface to be determined or the surface regions to be irradiated by PDT are emphasized in the image of the fundus for the physician. For this purpose, the EMS in transmission 14.1 in the partial system 2.2 is controlled in such a way that it marks the elements associated with the therapy surface for monitoring for the physician in the irradiated plane 4.1 in color or in a blinking manner (e.g., color marking by SM 15 or blinking intensity marking). The physician can change the therapy surface interactively in any way. The start of therapy radiation, e.g., for PDT, is carried out by introducing the swing-out mirror 8.6 into the partial system 2.2 and switching on the therapy laser 9.2. At the same time, the elements of the EMS in transmission 14.1 in the partial system 2.2 which previously let through the marking beams for the surface to receive therapy now let through the therapy beams, wherein the transmission of the elements can be varied for fine tuning.

Previous problems due to eye movements which can shift the site to be irradiated during the irradiation period are overcome in that the surface to be irradiated is continuously tracked by means of the EMS in transmission 14.1 in the partial system 2.2. This is achieved in that the described infrared beam paths whose image sequences are evaluated by image analysis and supply the correction values for tracking. Images for evaluation of eye movements are prepared by additional preferably simultaneous beam paths realized by programming technique. The displacement coordinates conditioned by eye movement are used directly for correcting the therapy surface position or for switching off or interrupting therapy.

Laser Coagulation

In this case also, coagulation can be carried out by laser according to the invention with high functional adaptivity interactively or automatically alternately between examinations and therapy. As was already described, the surfaces to be coagulated can be marked manually by the physician or corresponding to therapy criteria based on examination results in the image (monitor or through generation of additional marked beam path). It is also assumed in this case that criteria can be defined for the treatment site which can be found and marked automatically by corresponding examination programs and processes. The laser coagulation is carried out after the coagulation beam path from FIG. 9b is mirrored into the irradiation system 2 by means of swing-out mirrors 8.6, by controlling the x-y scanner mirror 8.10 (adjustment of the coagulation site in the irradiated plane 4.1), by adjusting focus by means of optics unit 8.4 (defective vision compensation) and by controlling the therapy laser 9.2. The control coordinates are given manually by the physician or automatically and are made visible in the described manner by means of an auxiliary beam path to be generated in addition (e.g., by means of partial system 2.2). The laser shot is triggered by the physician or according to criteria which can be determined beforehand so as to be monitored by the physician. Within the meaning of functional adaptivity, the tracking program (follower program) described above can again be called up by programming technique with the corresponding additional beam paths, the eye movements can be detected and the adjusted coagulation coordinates can be automatically tracked or the laser shot can be blocked. Another essential advantage in addition to the advantages of individually adaptive therapy, already described, consists in that coagulation can be carried out in the area of the macula near the vision center under extensive monitoring of hazardous eye movements.

Apart from other kinds of measurements of the fundus, further areas of use for the invention within the framework of multifunctionality are vision testing, refractometry, perimetry and microperimetry with monitoring of the fundus and correction for eye movement, examination of fixation disturbances, ophthalmologic spectrometry, use as abberometer or as fundus-monitored stimulator for electrophysiology, and high-resolution retinal documentation and topology. In this connection, it may be required to provide apparatuses according to the invention with additional partial systems such as for image recording of the pupil plane of the eye.

The apparatuses and methods according to the invention have considerable advantages particularly for uses of topology, that is, for acquisition of height and depth as well as changes in the latter. The optional programming of elemental beam bundles makes it possible to generate any light sections in the eye 10. By means of additional free control of the individual elements of a CCD receiver 13.1, the light sections can be optionally scanned with respect to depth and information can be obtained from directly illuminated volume elements on the eye 10 as well as indirectly illuminated volume elements depending on the control of the pixels to be read out. In this connection, images can also be prepared from different planes of the eye 10. In contrast to known methods, these sections can also be examined spectrally.

While the foregoing description and drawings represent the present invention, it will be obvious to those skilled in the art that various changes may be made therein without departing from the true spirit and scope of the present invention.

REFERENCE NUMBERS

1 reception system
1.1 to 1.n partial systems of the reception system
2 irradiation system
2.1 to 2.n partial systems of the irradiation system
3 reception-side object plane and image plane
3.1 object plane
3.2 image plane or receiver plane conjugate to 3.1
3.2 to 3.n planes conjugate to 3.1
4 irradiation-side object plane and image plane
4.1 irradiated plane
4.2 to 4.n planes conjugate to 4.1
5.1 to 5.n pupil planes of the reception system
6.1 to 6.n pupil planes with respect to the irradiated plane
7.1 to 7.n reception-side optics units
8.1 to 8.5 irradiation-side optics units
8.6 swing-out mirror
8.7 deflecting mirror
8.8 partially transparent mirror
8.9 spectral splitter
8.10 xy scanner mirror
9 irradiation source
9.1 infrared source
9.2 therapy laser, e.g., for PDT
9.3 coagulation laser or measurement laser
10 eye
11 ophthalmoscope lens
12 beam splitter for splitting 1 and 2
13 receiver outside of EMS receiver
13.1 CCD receiver
13.2 infrared image receiver
14 beam manipulation unit (EMS) with independently controllable elements
14.1 EMS in transmission
14.2 EMS in reflection
14.3 EMS in emission
14.4 EMS as receiver
15 beam manipulator (SM)
16 interface
17 information technology system (ITS)
17.1 control units
17.2 data, signal and/or image storage units
17.3 signal processing and/or image processing units
17.4 evaluating units
17.5 central unit
17.6 units for dialog operation and results presentation
17.7 program library
17.8 units for results documentation

The invention claimed is:

1. An apparatus comprising:
an irradiation system generating an irradiated plane with at least one pupil plane with respect to the irradiated plane;
a reception system for imaging an object plane in at least one plane conjugate thereto;
said reception system having at least one pupil plane which is the plane of an aperture diaphragm or a plane conjugate thereto; and
at least two beam manipulation units being arranged in one of the above-mentioned planes, each beam manipulation unit being connected by an interface to an information technology system, which controls the elements of the beam manipulation units with respect to time and location in order to manipulate the characteristics of the radiation in such a way that different beam paths (elemental beam bundles) can be generated by programming.

2. The apparatus according to claim 1, wherein at least two beam manipulation units are arranged in the reception system, wherein one beam manipulation unit is arranged in a plane conjugate to the object plane and another beam manipulation unit is arranged in a pupil plane of the reception system.

3. The apparatus according to claim 1, wherein at least two beam manipulation units are arranged in the irradiation system, wherein one beam manipulation unit is arranged in a plane conjugate to the irradiated plane and at least one other beam manipulation unit is arranged in a pupil plane with respect to the irradiated plane.

4. The apparatus according to claim 1, wherein at least two beam manipulation units are arranged in the reception system, wherein at least one beam manipulation unit is arranged in a plane conjugate to the object plane and at least a second beam manipulation unit is arranged in a pupil plane of the reception system, and wherein two additional beam manipulation units are arranged in the irradiation system, wherein one beam manipulation unit is arranged in a plane conjugate to the irradiated plane and at least one other beam manipulation unit is arranged in a pupil plane with respect to the irradiated plane.

5. The apparatus according to claim 1, wherein a conventional irradiation source is in continuous operation, and wherein a means is provided for temporarily coupling a flash lamp into the irradiation system.

6. The apparatus according to claim 1, wherein the information technology system comprises control units which are connected by interfaces to the controllable units of the apparatus, including the receiver, on the one hand and are connected on the other hand to a central unit communicating in turn with signal processing and image processing units, with evaluating units, with signal storage and image storage units, with a program library, a patient-specific database, and units for dialog operation and results presentation.

7. A method for the operation of an apparatus according to claim 1, comprising:
    forming elemental beam bundles by controlling the elements of the beam manipulation units with respect to time and location, and assigning different function-determining characteristics to these elemental beam bundles, so that the elemental beam bundles can be allocated individually or in groups to a large number of different beam paths which can be generated by programming and which have different functions for different methods of imaging, measuring, testing, stimulation or therapy realized simultaneously and/or successively.

8. The method according to claim 7, wherein different characteristics are assigned to the individual beam paths by controlling the beam manipulation units and the other controllable means, which characteristics are suitable for separating the individual beam paths from one another with respect to information by signal analysis or image analysis.

9. The method according to claim 7, wherein the function-determining characteristics can be the location, the geometric shape and surface in the irradiated plane, in the pupil plane and in the receiver-active object plane, and the position of these planes, the intensity, modulation frequency, radiating direction, quantity of bundles per beam path, spectral characteristics, polarization characteristics and time sequence characteristics, and wherein essential characteristics of the respective examination and treatment are determined by these function-determining characteristics.

10. The method according to claim 9, wherein the function-determining characteristics, effective location in the plane and along the depth, effective surface, time sequence and dosage for the treatment with light can be configured by programming and can be combined simultaneously or successively with other testing, imaging, measuring, testing and stimulating functions.

11. The method according to claim 7, wherein the formation of elemental beam bundles, the allocation of characteristics and physical beam paths, and the evaluating software can be changed in any way through programming during an examination process depending on intermediate results or by dialog mode control corresponding to function determination.

12. The method according to claim 11, wherein the feedback signals from intermediate results of an examination process or from examination results of other examinations with other functions of the device are formed in timed sequence or simultaneously by the information technology system which, in cooperation with optimizing programs, can optimize individual functions, also therapeutic functions, with respect to distinctive aspects of the patient and/or of the interview and/or of the examiner the examination process and the adjustments (characteristics) of the apparatus for the respective function before and/or during and/or after the examination process for current or subsequent examinations.

13. The method according to claim 12, wherein all of the actual adjustments and optimized changes for repetitive examinations are stored in a patient-specific, examiner-specific and examination-specific manner.

14. The method according to claim 13, wherein displacement coordinates of moving objects are determined from signal data or image data and are used as correction signals by means of beam manipulation unit control for correcting the elemental beam bundles or for assessing or evaluating examination results.

15. The method according to claim 7, wherein an examination process proceeds by the following steps:
    step A: defining the goal of the examination and, therefore, of the necessary functional beam paths and their desired system parameters and function for the device principle to be realized with corresponding program call;
    step B: selecting and calling of the program for controlling startup and running, for signal analysis and image analysis, evaluation, dialog operation, functional and individual optimization, for patient-related storage, documentation and results presentation;
    step C: program-controlled basic adjustment—1st examination period further comprising the steps of:
    determining the position of the imaging-side object plane and of the irradiated plane in the eye for the initial starting point by controlling the optics units for focusing and defective vision compensation, said optics units serving at the same time as means for displacement of the imaging-side object plane and the irradiated plane in the depth of the eye and for changing the imaging scale;
    adjusting the position and geometry of the intersection points of the elemental beam bundles of the individual beam paths for the imaging-side object plane in the eye through control and readout of the elements of the corresponding receiver unit(s) in the receiver plane or image plane conjugate to the object plane in the individual reception-side beam paths and/or through adjustment of magnification by means of the second displaceable optics unit;
    adjusting the position and geometry of the intersection points of the elemental beam bundles of the individual beam paths for the irradiated plane by controlling the elements of the corresponding beam manipulation unit in a plane conjugate to the irradiated plane;
    adjusting the position and geometry of the intersection points of the elemental beam bundles of the individual beam paths through the plane of the eye pupil by controlling the elements of the corresponding beam manipulation unit in a plane conjugate to the eye pupil;

allocating the elemental beam bundles to functional beam paths and assignment of the characteristics already described by intensity, color, degree of polarization, frequency to characteristics corresponding to the provided controllable means of the arrangement;

processing the programs for signal analysis and image analysis, evaluation, dialog operation, functional and individual optimization, for patient-related storage, documentation and presentation of results for the current processing period; and step D: controlling the examination process through repetition of the periods (step C) by varying the adjustment in the first five substeps and implementing the 6th substep until the examination process is concluded.

16. An apparatus comprising:
an irradiation system generating an irradiated plane with at least one pupil plane with respect to the irradiated plane;
a reception system for imaging an object plane in at least one plane conjugate thereto;
at least one pupil plane of the reception system which is the plane of an aperture diaphragm or a plane conjugate thereto;
a beam splitter being provided for combining the irradiation system and the reception system and in which the pupil planes with respect to the irradiated plane and the pupil planes of the reception system are planes which are conjugate to one another; and
at least one beam manipulation unit being arranged in one of the above-mentioned planes, said beam manipulation unit being connected by an interface information technology system, which controls the elements of the beam manipulation unit with respect to time and location in order to manipulate the characteristics of the radiation in such a way that different beam paths (elemental beam bundles) can be generated by programming.

17. The apparatus according to claim 16, wherein at least two beam manipulation unit are arranged in the reception system, wherein one beam manipulation unit is arranged in a plane conjugate to the object plane and another beam manipulation unit is arranged in a pupil plane of the reception system.

18. The apparatus according to claim 16, wherein at least two beam manipulation units are arranged in the irradiation system, wherein one beam manipulation unit is arranged in a plane conjugate to the irradiated plane and at least one other beam manipulation unit is arranged in a pupil plane with respect to the irradiated plane.

19. The apparatus according to claim 16, wherein at least two beam manipulation units are arranged in the reception system, wherein at least one beam manipulation unit is arranged in a plane conjugate to the object plane and at least a second beam manipulation unit is arranged in a pupil plane of the reception system, and wherein two additional beam manipulation units are arranged in the irradiation system, and wherein one beam manipulation unit is arranged in a plane conjugate to the irradiated plane and at least one other beam manipulation unit is arranged in a pupil plane with respect to the irradiated plane.

20. The apparatus according to claim 16, wherein the beam splitter is constructed as the beam manipulation units.

21. The apparatus according to claim 16, wherein a conventional irradiation source is in continuous operation, and wherein a means is provided for temporarily coupling a flash lamp into the irradiation system.

22. The apparatus according to claim 16, wherein the information technology system comprises control units which are connected by interfaces to the controllable units of the apparatus, including the receiver, on the one hand and are connected on the other hand to a central unit communicating in turn with signal processing and image processing units, with evaluating units, with signal storage and image storage units, with a program library, a patient-specific database, and units for dialog operation and results presentation.

23. A method for the operation of an apparatus according to claim 16, comprising:
forming elemental beam bundles by controlling the elements of the beam manipulation unit with respect to time and location, and assigning different function-determining characteristics to these elemental beam bundles, so that the elemental beam bundles can be allocated individually or in groups to a large number of different beam paths which can be generated by programming and which have different functions for different methods of imaging, measuring, testing, stimulation or therapy realized simultaneously and/or successively.

24. The method according to claim 23, wherein different characteristics are assigned to the individual beam paths by controlling the beam manipulation unit and the other controllable means, which characteristics are suitable for separating the individual beam paths from one another with respect to information by signal analysis or image analysis.

25. The method according to claim 23, wherein the function-determining characteristics can be the location, the geometric shape and surface in the irradiated plane, in the pupil plane and in the receiver-active object plane, and the position of these planes, the intensity, modulation frequency, radiating direction, quantity of bundles per beam path, spectral characteristics, polarization characteristics and time sequence characteristics, and wherein essential characteristics of the respective examination and treatment are determined by these function-determining characteristics.

26. The method according to claim 25, wherein the function-determining characteristics, effective location in the plane and along the depth, effective surface, time sequence and dosage for the treatment with light can be configured by programming and can be combined simultaneously or successively with other testing, imaging, measuring, testing and stimulating functions.

27. The method according to claim 23, wherein the formation of elemental beam bundles, the allocation of characteristics and physical beam paths, and the evaluating software can be changed in any way through programming during an examination process depending on intermediate results or by dialog mode control corresponding to function determination.

28. The method according to claim 27, wherein the feedback signals from intermediate results of an examination process or from examination results of other examinations with other functions of the device are formed in timed sequence or simultaneously by the information technology system which, in cooperation with optimizing programs, can optimize individual functions, also therapeutic functions, with respect to distinctive aspects of the patient and/or of the interview and/or of the examiner the examination process and the adjustments (characteristics) of the apparatus for the respective function before and/or during and/or after the examination process for current or subsequent examinations.

29. The method according to claim 28, wherein all of the actual adjustments and optimized changes for repetitive examinations are stored in a patient-specific, examiner-specific and examination-specific manner.

30. The method according to claim 29, wherein displacement coordinates of moving objects are determined from signal data or image data and are used as correction signals by means of beam manipulation unit control for correcting the elemental beam bundles or for assessing or evaluating examination results.

31. The method according to claim 23, wherein an examination process proceeds by the following steps:

step A: defining the goal of the examination and, therefore, of the necessary functional beam paths and their desired system parameters and function for the device principle to be realized with corresponding program call;

step B: selecting and calling of the program for controlling startup and running, for signal analysis and image analysis, evaluation, dialog operation, functional and individual optimization, for patient-related storage, documentation and results presentation;

step C: program-controlled basic adjustment—1st examination period further comprising the steps of:

determining the position of the imaging-side object plane and of the irradiated plane in the eye for the initial starting point by controlling the optics units for focusing and defective vision compensation, said optics units serving at the same time as means for displacement of the imaging-side object plane and the irradiated plane in the depth of the eye and for changing the imaging scale;

adjusting the position and geometry of the intersection points of the elemental beam bundles of the individual beam paths for the imaging-side object plane in the eye through control and readout of the elements of the corresponding receiver unit(s) in the receiver plane or image plane conjugate to the object plane in the individual reception-side beam paths and/or through adjustment of magnification by means of the second displaceable optics unit;

adjusting the position and geometry of the intersection points of the elemental beam bundles of the individual beam paths for the irradiated plane by controlling the elements of the corresponding beam manipulation unit in a plane conjugate to the irradiated plane;

adjusting the position and geometry of the intersection points of the elemental beam bundles of the individual beam paths through the plane of the eye pupil by controlling the elements of the corresponding beam manipulation unit in a plane conjugate to the eye pupil;

allocating the elemental beam bundles to functional beam paths and assignment of the characteristics already described by intensity, color, degree of polarization, frequency to characteristics corresponding to the provided controllable means of the arrangement;

processing the programs for signal analysis and image analysis, evaluation, dialog operation, functional and individual optimization, for patient-related storage, documentation and presentation of results for the current processing period; and step D: controlling the examination process through repetition of the periods (step C) by varying the adjustment in the first five substeps and implementing the 6th substep until the examination process is concluded.

32. An ophthalmologic examination device composing:

an irradiation system generating an irradiated plane with at least one pupil plane with respect to the irradiated plane;

a reception system for imaging an object plane in at least one plane conjugate thereto;

at least one pupil plane of the reception system which is the plane of an aperture diaphragm or a plane conjugate thereto;

a beam splitter being provided which combines the irradiation system and the reception system and guides them into the eye by a shared ophthalmologic lens;

the pupil planes with respect to the irradiated plane and the pupil planes of the reception system being planes which are conjugate to one another and to the pupil of the eye;

at least one beam manipulation unit being arranged in one of the above-mentioned planes, said beam manipulation unit being connected by an interface to an information technology system, which controls the elements of the beam manipulation unit with respect to time and location in order to manipulate the characteristics of the radiation in such a way that different beam paths (elemental beam bundles) can be generated through programming.

33. The apparatus according to claim 32, wherein at least two beam manipulation units are arranged in the reception system, wherein one beam manipulation unit is arranged in a plane conjugate to the object plane and another beam manipulation unit is arranged in a pupil plane of the reception system.

34. The apparatus according to claim 32, wherein at least two beam manipulation units are arranged in the irradiation system, wherein one beam manipulation unit is arranged in a plane conjugate to the irradiated plane and at least one other beam manipulation unit is arranged in a pupil plane with respect to the irradiated plane.

35. The apparatus according to claim 32, wherein at least two beam manipulation units are arranged in the reception system, wherein at least one beam manipulation unit is arranged in a plane conjugate to the object plane and at least a second beam manipulation unit is arranged in a pupil plane of the reception system, and wherein two additional beam manipulation units are arranged in the irradiation system, wherein one beam manipulation unit is arranged in a plane conjugate to the irradiated plane and at least one other beam manipulation unit is arranged in a pupil plane with respect to the irradiated plane.

36. The apparatus according to claim 32, wherein the beam splitter is constructed as the beam manipulation units.

37. The apparatus according to claim 32, wherein a conventional irradiation source is in continuous operation, and wherein a means is provided for temporarily coupling a flash lamp into the irradiation system.

38. The apparatus according to claim 32, wherein optical means are provided for coupling an additional therapy beam into the irradiation system, which additional therapy beam irradiates an beam manipulation unit in a plane conjugate to the irradiated plane, wherein these means are controllable, wherein the therapy beam is used for AMD treatment by means of a therapeutically acting laser, wherein means for the uniform illumination of the optically active total surface of the beam manipulation unit or of a known partial surface of the beam manipulation unit are provided in this additional therapy beam path, and wherein the therapeutically acting laser is controllable in intensity.

39. The apparatus according to claim 32, wherein means are provided for temporarily switching on another additional irradiation in the irradiation system in a controllable manner, wherein optical means are provided in this additional irradiation for generating another pupil plane conjugate to the eye pupil and for focusing a parallel light bundle in the irradiated plane, wherein a controllable unit for x-y deflection of the parallel light bundle is arranged in this other pupil plane, and wherein a laser with controllable intensity and pulse energy is provided as source.

40. The apparatus according to claim 32, wherein the information technology system comprises control units which are connected by interfaces to the controllable units of the apparatus, including the receiver, on the one hand and are connected on the other hand to a central unit communicating in turn with signal processing and image processing units, with evaluating units, with signal storage and image storage units, with a program library, a patient-specific database, and units for dialog operation and results presentation.

41. A method for the operation of an apparatus according to claim 32, comprising:
   forming elemental beam bundles by controlling the elements of the beam manipulation unit with respect to time and location, and assigning different function-determining characteristics to these elemental beam bundles, so that the elemental beam bundles can be allocated individually or in groups to a large number of different beam paths which can be generated by programming and which have different functions for different methods of imaging, measuring, testing, stimulation or therapy realized simultaneously and/or successively.

42. The method according to claim 41, wherein different characteristics are assigned to the individual beam paths by controlling the beam manipulation unit and the other controllable means, which characteristics are suitable for separating the individual beam paths from one another with respect to information by signal analysis or image analysis.

43. The method according to claim 41, wherein the function-determining characteristics can be the location, the geometric shape and surface in the irradiated plane, in the pupil plane and in the receiver-active object plane, and the position of these planes, the intensity, modulation frequency, radiating direction, quantity of bundles per beam path, spectral characteristics, polarization characteristics and time sequence characteristics, and wherein essential characteristics of the respective examination and treatment are determined by these function-determining characteristics.

44. The method according to claim 43, wherein the function-determining characteristics, effective location in the plane and along the depth, effective surface, time sequence and dosage for the treatment with light can be configured by programming and can be combined simultaneously or successively with other testing, imaging, measuring, testing and stimulating functions.

45. The method according to claim 41, wherein the formation of elemental beam bundles, the allocation of characteristics and physical beam paths, and the evaluating software can be changed in any way through programming during an examination process depending on intermediate results or by dialog mode control corresponding to function determination.

46. The method according to claim 45, wherein the feedback signals from intermediate results of an examination process or from examination results of other examinations with other functions of the device are formed in timed sequence or simultaneously by the information technology system which, in cooperation with optimizing programs, can optimize individual functions, also therapeutic functions, with respect to distinctive aspects of the patient and/or of the interview and/or of the examiner the examination process and the adjustments (characteristics) of the apparatus for the respective function before and/or during and/or after the examination process for current or subsequent examinations.

47. The method according to claim 46, wherein all of the actual adjustments and optimized changes for repetitive examinations are stored in a patient-specific, examiner-specific and examination-specific manner.

48. The method according to claim 47, wherein displacement coordinates of moving objects are determined from signal data or image data and are used as correction signals by means of the beam manipulation unit control for correcting the elemental beam bundles or for assessing or evaluating examination results.

49. The method according to claim 41, wherein an examination process proceeds by the following steps:
   step A: defining the goal of the examination and, therefore, of the necessary functional beam paths and their desired system parameters and function for the device principle to be realized with corresponding program call;
   step B: selecting and calling of the program for controlling startup and running, for signal analysis and image analysis, evaluation, dialog operation, functional and individual optimization, for patient-related storage, documentation and results presentation;
   step C: program-controlled basic adjustment—1st examination period further comprising the steps of:
   determining the position of the imaging-side object plane and of the irradiated plane in the eye for the initial starting point by controlling the optics units for focusing and defective vision compensation, said optics units serving at the same time as means for displacement of the imaging-side object plane and the irradiated plane in the depth of the eye and for changing the imaging scale;
   adjusting the position and geometry of the intersection points of the elemental beam bundles of the individual beam paths for the imaging-side object plane in the eye through control and readout of the elements of the corresponding receiver unit(s) in the receiver plane or image plane conjugate to the object plane in the individual reception-side beam paths and/or through adjustment of magnification by means of the second displaceable optics unit;
   adjusting the position and geometry of the intersection points of the elemental beam bundles of the individual beam paths for the irradiated plane by controlling the elements of the corresponding beam manipulation unit in a plane conjugate to the irradiated plane;
   adjusting the position and geometry of the intersection points of the elemental beam bundles of the individual beam paths through the plane of the eye pupil by controlling the elements of the corresponding beam manipulation unit in a plane conjugate to the eye pupil;
   allocating the elemental beam bundles to functional beam paths and assignment of the characteristics already described by intensity, color, degree of polarization, frequency to characteristics corresponding to the provided controllable means of the arrangement;
   processing the programs for signal analysis and image analysis, evaluation, dialog operation, functional and individual optimization, for patient-related storage, documentation and presentation of results for the current processing period; and
   step D: controlling the examination process through repetition of the periods (step C) by varying the adjustment in the first five substeps and implementing the 6th substep until the examination process is concluded.

* * * * *